(12) United States Patent
Park et al.

(10) Patent No.: US 11,788,095 B2
(45) Date of Patent: Oct. 17, 2023

(54) SYNTHETIC PROMOTER BASED ON GENE FROM ACID-RESISTANT YEAST

(71) Applicant: SK INNOVATION CO., LTD., Seoul (KR)

(72) Inventors: Jae Yeon Park, Daejeon (KR); Ki Sung Lee, Daejeon (KR); Tae Young Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/454,339

(22) Filed: Nov. 10, 2021

(65) Prior Publication Data

US 2022/0145310 A1    May 12, 2022

(30) Foreign Application Priority Data

Nov. 12, 2020 (KR) .................. 10-2020-0150964

(51) Int. Cl.
| | |
|---|---|
| *C12N 15/81* | (2006.01) |
| *C12N 1/16* | (2006.01) |
| *C12N 9/88* | (2006.01) |
| *C12P 7/56* | (2006.01) |
| *C12R 1/72* | (2006.01) |
| *C12R 1/865* | (2006.01) |

(52) U.S. Cl.
CPC ............ *C12N 15/815* (2013.01); *C12N 1/16* (2013.01); *C12N 9/88* (2013.01); *C12P 7/56* (2013.01); *C12R 2001/72* (2021.05); *C12R 2001/865* (2021.05); *C12Y 401/01001* (2013.01)

(58) Field of Classification Search
CPC .......... C12N 15/815; C12N 1/16; C12N 9/88; C12N 15/81; C12N 9/0006; C12N 9/1025; C12N 2830/008; C12N 2830/15; C12P 7/56; C12R 2001/72; C12R 2001/865; C12Y 401/01001; C12Y 101/01001; C12Y 101/01027; C12Y 101/01028; C12Y 203/03001; C07K 14/39

See application file for complete search history.

(56) References Cited

U.S. PATENT DOCUMENTS

| | | |
|---|---|---|
| 10,280,427 B2 | 5/2019 | Chang et al. |
| 11,339,398 B2 * | 5/2022 | Park ............... C12N 9/0006 |
| 2015/0203880 A1 | 7/2015 | Stephanopoulos et al. |
| 2016/0160299 A1 * | 6/2016 | Alper ............... C12N 15/80 506/10 |
| 2021/0324346 A1 | 10/2021 | Park et al. |
| 2021/0403882 A1 | 12/2021 | Park et al. |
| 2022/0056459 A1 | 2/2022 | Park et al. |

FOREIGN PATENT DOCUMENTS

| | | |
|---|---|---|
| CA | 2048676 C | 4/2000 |
| KR | 10-0468482 B1 | 1/2005 |
| KR | 10-2019-0121030 A | 10/2019 |
| KR | 10-2019-0121031 A | 10/2019 |
| KR | 10-2020-0040017 A | 4/2020 |
| KR | 10-2140596 B1 | 8/2020 |
| KR | 10-2140597 B1 | 8/2020 |
| KR | 1020210128742 A | 10/2021 |
| KR | 1020210158676 A | 12/2021 |
| WO | 9109956 A1 | 7/1991 |
| WO | 2019203436 A1 | 10/2019 |
| WO | 2020075986 A2 | 4/2020 |

OTHER PUBLICATIONS

Karlin, et al. "Applications and statistics for multiple high-scoring segments in molecular sequences," Proc. Natl. Acad.Sci. USA, 90, 5873-5877 (1993).
Blazeck et al., "Controlling promoter strength and regulation in *Saccharomyces cerevisiae* using synthetic hybrid promoters," Biotechnology and Bioengineering, 109(11):2884-2895 (2012).
Rajkumar et al., "Engineering of synthetic, stress-responsive yeast promoters," Nucleic Acids Research, 44(17); e136 (2016).

* cited by examiner

*Primary Examiner* — Ganapathirama Raghu
(74) *Attorney, Agent, or Firm* — THE WEBB LAW FIRM

(57) ABSTRACT

The present invention relates to a synthetic promoter capable of controlling the expression of a target gene at various locations in the genome of an acid-resistant strain, and more particularly to a synthetic promoter including a core promoter derived from an acid-resistant strain and an upstream activating sequence (UAS) element serving as an enhancer. When the present invention is applied to a variety of genetic and metabolic engineering techniques for acid-resistant yeast, various metabolic networks can be configured as desired while controlling the expression level of the target gene, so a method of producing various metabolites using acid-resistant yeast is provided, and the cost of producing the metabolites can be greatly reduced depending on the properties of the acid-resistant yeast.

10 Claims, 6 Drawing Sheets

Specification includes a Sequence Listing.

SEQUENCE LISTING

<160> NUMBER OF SEQ ID NOS: 34

<210> SEQ ID NO 1
<211> LENGTH: 174
<212> TYPE: DNA
<213> ORGANISM: Artificial Sequence
<220> FEATURE:
<223> OTHER INFORMATION: ADH gene (g4423) core promoter (allele 1)

<400> SEQUENCE: 1
tatataaatg caattaattg attgttcctg tcacataatt ttttttgttt gttacccttta      60 ttctttatcc atttaatta tttcttgtat ctttcttttc tatttctctt ttctgtttaa      120
tctcaccgta cacatatata tccatatatc aatacaaata aaaatcattt aaaa           174

<210> SEQ ID NO 2
<211> LENGTH: 174
<212> TYPE: DNA
<213> ORGANISM: Artificial Sequence
<220> FEATURE:
<223> OTHER INFORMATION: ADH gene (g4423) core promoter (allele 2)

<400> SEQUENCE: 2
tatataaatg caattaattg attgttcctg tcacataatt ttttttgttt gttaccttta      60
ttctttatcc atttagttta gttcttatat ctttcttttc tatttctctt tttcgtttaa    120
tctcaccgta cacatatata tccatatatc aatacaaata aaaatcattt aaaa           174

<210> SEQ ID NO 3
<211> LENGTH: 275
<212> TYPE: DNA
<213> ORGANISM: Artificial Sequence
<220> FEATURE:
<223> OTHER INFORMATION: UAS : CIT

<400> SEQUENCE: 3
tagagattac tacatattcc aacaagacct tcgcaggaaa gtatacctaa actaattaaa      60
gaaatctccg aagttcgcat ttcattgaac ggctcaatta atctttgtaa atatgagcgt    120
ttttacgttc acattgcctt tttttttatg tatttacctt gcattttgt gctaaaaggc     180 gtcacgtttt tttccgccgc agccgccgg aaatgaaaag tatgacccccc gctagaccaa    240

```
aaatactttt gtgttattgg aggatcgcaa tccct                              275
```

<210> SEQ ID NO 4
<211> LENGTH: 240
<212> TYPE: DNA
<213> ORGANISM: Artificial Sequence
<220> FEATURE:
<223> OTHER INFORMATION: UAS : CLB

<400> SEQUENCE: 4

```
agtggaatta ttagaatgac cactactcct tctaatcaaa cacgcggaaa tagccgccaa    60
aagacagatt ttattccaaa tgcgggtaac tatttgtata atatgtttac atattgagcc   120
cgtttaggaa agtgcaagtt caaggcacta atcaaaaaag gagatttgta aatatagcga   180
ccgaatcagg aaaaggtcaa caacgaagtt cgcgatatgg atgaacttcg gtgcctgtcc   240
```

<210> SEQ ID NO 5
<211> LENGTH: 766
<212> TYPE: DNA
<213> ORGANISM: Artificial Sequence
<220> FEATURE:
<223> OTHER INFORMATION: 2CIT-pg4423

<400> SEQUENCE: 5

```
tagagattac tacatattcc aacaagacct tcgcaggaaa gtatacctaa actaattaaa    60
gaaatctccg aagttcgcat ttcattgaac ggctcaatta atctttgtaa atatgagcgt   120
ttttacgttc acattgcctt ttttttttatg tatttacctt gcattttttgt gctaaaaggc   180
gtcacgttttt tttccgccgc agccgcccgg aaatgaaaag tatgaccccc gctagaccaa   240
aaatactttt gtgttattgg aggatcgcaa tccctactag ttagagatta ctacatattc   300
caacaagacc ttcgcaggaa agtatacctaa aactaattaa agaaatctcc gaagttcgca   360
tttcattgaa cggctcaatt aatctttgta aatatgagcg ttttttacgtt cacattgcct   420
tttttttttat gtatttacct tgcattttttg tgctaaaagg cgtcacgttt ttttccgccg   480
cagccgcccg gaaatgaaaa gtatgaccccc cgctagacca aaaatactttt tgtgttattg   540
gaggatcgca atccctgtcg actttcttat aatttttatc aattaccaaa tatatataaa   600
tgcaattaat tgattgttcc tgtcacataa ttttttttgt ttgttacctt tattctttat   660
ccatttaatt tatttcttgt atctttcttt tctatttctc tttttctgtttt aatctcaccg   720
tacacatata tatccatata tcaatacaaa taaaaatcat ttaaaa                   766
```

<210> SEQ ID NO 6
<211> LENGTH: 2030
<212> TYPE: DNA
<213> ORGANISM: Artificial Sequence
<220> FEATURE:
<223> OTHER INFORMATION: 2CIT-pg4423-BtLDH-CYC1t

<400> SEQUENCE: 6

```
tagagattac tacatattcc aacaagacct tcgcaggaaa gtatacctaa actaattaaa    60
gaaatctccg aagttcgcat ttcattgaac ggctcaatta atctttgtaa atatgagcgt   120
ttttacgttc acattgcctt ttttttttatg tatttacctt gcattttttgt gctaaaaggc   180
gtcacgttttt tttccgccgc agccgcccgg aaatgaaaag tatgaccccc gctagaccaa   240
aaatactttt gtgttattgg aggatcgcaa tccctactag ttagagatta ctacatattc   300
caacaagacc ttcgcaggaa agtatacctaa aactaattaa agaaatctcc gaagttcgca   360
tttcattgaa cggctcaatt aatctttgta aatatgagcg ttttttacgtt cacattgcct   420
```

```
tttttttttat gtatttacct tgcattttttg tgctaaaagg cgtcacgttt ttttccgccg      480
cagccgcccg gaaatgaaaa gtatgaccccc cgctagacca aaaatacttt tgtgttattg      540
gaggatcgca atccctgtcg actttcttat aattttttatc aattaccaaa tatatataaa      600
tgcaattaat tgattgttcc tgtcacataa ttttttttgt ttgttacctt tattctttat      660
ccatttaatt tatttcttgt atctttcttt tctatttctc ttttctgttt aatctcaccg      720
tacacatata tatccatata tcaatacaaa taaaaatcat ttaaaagaat tcaacaaaat      780
ggctactttg aaagatcaat tgattcaaaa tttgttgaaa gaagaacatg ttccacaaaa      840
taaaattact attgttggtg ttggtgctgt tggtatggct tgtgctattt ctattttgat      900
gaaagatttg gctgatgaag ttgctttggt tgatgttatg aagataaat tgaaaggtga      960 aatgatggat ttgcaacatg gttctttgtt tttgagaact ccaaaaattg tttctggtaa     1020
agattataat gttactgcta attctagatt ggttattatt actgctggtg ctagacaaca     1080
agaaggtgaa tctagattga atttggttca agaaatgtt aatatttta aatttattat     1140 tccaaatatt gttaaatatt ctccaaattg taaattgttg gttgtttcta atccagttga     1200
tattttgact tatgttgctt ggaaaatttc tggttttcca aaaaatagag ttattggttc     1260
tggttgtaat ttggattctg ctagatttag atatttgatg ggtgaaagat tgggtgttca     1320
tccattgtct tgtcatggtt ggattttggg tgaacatggt gattcttctg ttccagtttg     1380
gtctggtgtt aatgttgctg gtgttcttt gaaaaatttg catccagaat tgggtactga     1440
tgctgataaa gaacaatgga aagctgttca taaacaagtt gttgattctg cttatgaagt     1500
tattaaattg aaaggttata cttcttgggc tattggttg tctgttgctg atttggctga     1560
atctattatg aaaaatttga gaagagttca tccaatttct actatgatta aaggtttgta     1620
tggtattaaa gaagatgttt ttttgtctgt tccatgtatt ttgggtcaaa atggtatttc     1680
tgatgttgtt aaagttactt tgactcatga agaagaagct tgtttgaaaa aatctgctga     1740
tactttgtgg ggtattcaaa aagaattgca attttaactc gagtcatgta attagttatg     1800
tcacgcttac attcacgccc tccccccaca tccgctctaa ccgaaaagga aggagttaga     1860
caacctgaag tctaggtccc tatttatttt tttatagtta tgttagtatt aagaacgtta     1920
tttatatttc aaatttttct ttttttttctg tacagacgcg tgtacgcatg taacattata     1980
ctgaaaacct tgcttgagaa ggttttggga cgctcgaagg cttttaatttg            2030
```

<210> SEQ ID NO 7
<211> LENGTH: 1241
<212> TYPE: DNA
<213> ORGANISM: Artificial Sequence
<220> FEATURE:
<223> OTHER INFORMATION: 3CIT-pTEF1

<400> SEQUENCE: 7

```
tagagattac tacatattcc aacaagacct tcgcaggaaa gtatacctaa actaattaaa       60
gaaatctccg aagttcgcat ttcattgaac ggctcaatta atctttgtaa atatgagcgt      120
ttttacgttc acattgcctt ttttttttatg tatttacctt gcatttttgt gctaaaaggc      180
gtcacgtttt tttccgccgc agccgcccgg aaatgaaaag tatgaccccc gctagaccaa      240
aaatactttt gtgttattgg aggatcgcaa tccctactag ttagagatta ctacatattc      300
caacaagacc ttcgcaggaa agtatacca aactaattaa agaaatctcc gaagttcgca      360
tttcattgaa cggctcaatt aatctttgta aatatgagcg ttttttacgtt cacattgcct      420
```

| | |
|---|---|
| ttttttttat gtatttacct tgcatttttg tgctaaaagg cgtcacgttt ttttccgccg | 480 |
| cagccgcccg gaaatgaaaa gtatgacccc cgctagacca aaaatacttt tgtgttattg | 540 |
| gaggatcgca atccctgtcg actagagatt actacatatt ccaacaagac cttcgcagga | 600 |
| aagtatacct aaactaatta agaaatctc cgaagttcgc atttcattga acggctcaat | 660 |
| taatctttgt aaatatgagc gttttacgt tcacattgcc ttttttttta tgtatttacc | 720 |
| ttgcattttt gtgctaaaag gcgtcacgtt ttttccgcc gcagccgccc ggaaatgaaa | 780 |
| agtatgaccc ccgctagacc aaaaatactt tgtgttatt ggaggatcgc aatccctgag | 840 |
| ctcatagctt caaaatgttt ctactccttt tttactcttc cagatttct cggactccgc | 900 |
| gcatcgccgt accacttcaa acacccaag cacagcatac taaatttccc ctctttcttc | 960 |
| ctctaggtg tcgttaatta cccgtactaa aggtttggaa aagaaaaaag agaccgcctc | 1020 |
| gtttcttttt cttcgtcgaa aaaggcaata aaaattttta tcacgtttct ttttcttgaa | 1080 |
| aattttttt ttgattttt tctctttcga tgacctccca ttgatattta agttaataaa | 1140 |
| cggtcttcaa tttctcaagt ttcagttca ttttctttgt tctattacaa cttttttac | 1200 |
| ttcttgctca ttagaaagaa agcatagcaa tctaatctaa g | 1241 |

<210> SEQ ID NO 8
<211> LENGTH: 2527
<212> TYPE: DNA
<213> ORGANISM: Artificial Sequence
<220> FEATURE:
<223> OTHER INFORMATION: 3CIT-pTEF1-BtLDH-CYC1t

<400> SEQUENCE: 8

| | |
|---|---|
| tagagattac tacatattcc aacaagacct tcgcaggaaa gtatacctaa actaattaaa | 60 |
| gaaatctccg aagttcgcat tcattgaac ggctcaatta atctttgtaa atatgagcgt | 120 |
| ttttacgttc acattgcctt ttttttatg tatttacctt gcattttgt gctaaaaggc | 180 |
| gtcacgtttt ttccgccgc agccgccgg aaatgaaaag tatgacccc gctagaccaa | 240 |
| aaatactttt gtgttattgg aggatcgcaa tccctactag ttagagatta ctacatattc | 300 |
| caacaagacc ttcgcaggaa agtatacta aactaattaa agaaatctcc gaagttcgca | 360 |
| tttcattgaa cggctcaatt aatctttgta aatatgagcg ttttacgtt cacattgcct | 420 |
| tttttttat gtatttacct tgcatttttg tgctaaaagg cgtcacgttt ttttccgccg | 480 |
| cagccgcccg gaaatgaaaa gtatgacccc cgctagacca aaaatacttt tgtgttattg | 540 |
| gaggatcgca atccctgtcg actagagatt actacatatt ccaacaagac cttcgcagga | 600 |
| aagtatacct aaactaatta agaaatctc cgaagttcgc atttcattga acggctcaat | 660 |
| taatctttgt aaatatgagc gttttacgt tcacattgcc ttttttttta tgtatttacc | 720 |
| ttgcattttt gtgctaaaag gcgtcacgtt ttttccgcc gcagccgccc ggaaatgaaa | 780 |
| agtatgaccc ccgctagacc aaaaatactt tgtgttatt ggaggatcgc aatccctgag | 840 |
| ctcatagctt caaaatgttt ctactccttt tttactcttc cagatttct cggactccgc | 900 |
| gcatcgccgt accacttcaa acacccaag cacagcatac taaatttccc ctctttcttc | 960 |
| ctctaggtg tcgttaatta cccgtactaa aggtttggaa aagaaaaaag agaccgcctc | 1020 |
| gtttcttttt cttcgtcgaa aaaggcaata aaaattttta tcacgtttct ttttcttgaa | 1080 |
| aattttttt ttgattttt tctctttcga tgacctccca ttgatattta agttaataaa | 1140 |
| cggtcttcaa tttctcaagt ttcagttca ttttctttgt tctattacaa cttttttac | 1200 |
| ttcttgctca ttagaaagaa agcatagcaa tctaatctaa gttttctaga cccgggctgc | 1260 |

```
aggaattcaa caaaatggct actttgaaag atcaattgat tcaaaatttg ttgaaagaag    1320
aacatgttcc acaaaataaa attactattg ttggtgttgg tgctgttggt atggcttgtg    1380
ctatttctat tttgatgaaa gatttggctg atgaagttgc tttggttgat gttatggaag    1440
ataaattgaa aggtgaaatg atggatttgc aacatggttc tttgtttttg agaactccaa    1500
aaattgtttc tggtaaagat tataatgtta ctgctaattc tagattggtt attattactg    1560
ctggtgctag acaacaagaa ggtgaatcta gattgaattt ggttcaaaga atgttaata    1620
ttttttaaatt tattattcca atattgtta aatattctcc aaattgtaaa ttgttggttg    1680
tttctaatcc agttgatatt ttgacttatg ttgcttggaa atttctggt tttccaaaaa    1740
atagagttat tggttctggt tgtaatttgg attctgctag atttagatat ttgatgggtg    1800
aaagattggg tgttcatcca ttgtcttgtc atggttggat tttgggtgaa catggtgatt    1860
cttctgttcc agtttggtct ggtgttaatg ttgctggtgt ttcttttgaaa aatttgcatc    1920
cagaattggg tactgatgct gataaagaac aatggaaagc tgttcataaa caagttgttg    1980
attctgctta tgaagttatt aaattgaaag ttatacttc ttgggctatt ggtttgtctg    2040
ttgctgattt ggctgaatct attatgaaaa atttgagaag agttcatcca atttctacta    2100
tgattaaagg tttgtatggt attaaagaag atgtttttttt gtctgttcca tgtatttttgg    2160
gtcaaaatgg tatttctgat gttgttaaag ttactttgac tcatgaagaa gaagcttgtt    2220
tgaaaaaatc tgctgatact ttgtggggta ttcaaaaaga attgcaattt taactcgagt    2280
catgtaatta gttatgtcac gcttacattc acgccctccc cccacatccg ctctaaccga    2340
aaaggaagga gttagacaac ctgaagtcta ggtccctatt tatttttta tagttatgtt    2400
agtattaaga acgttattta tatttcaaat ttttctttttt tttctgtaca gacgcgtgta    2460
cgcatgtaac attatactga aaaccttgct tgagaaggtt ttgggacgct cgaaggcttt    2520
aatttgc                                                              2527
```

<210> SEQ ID NO 9
<211> LENGTH: 6770
<212> TYPE: DNA
<213> ORGANISM: Artificial Sequence
<220> FEATURE:
<223> OTHER INFORMATION: Plasmid 2CIT-pg4423-LpLDH-CYC1t

<400> SEQUENCE: 9

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaatttttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
```

-continued

```
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca agagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccta tgcggtgtga ataccgcac    1320
agatgcgtaa ggagaaaata ccgcatcagg aaattgtaaa cgttaatatt ttgttaaaat   1380
tcgcgttaaa ttttgttaa atcagctcat ttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc ccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggcgaa ttgggtacca cgtccgaggg ggccccgcaga aacctctcga   2040
gactagttag agattactac atattccaac aagaccttcg caggaaagta tacctaaact   2100
aattaaagaa atctccgaag ttcgcatttc attgaacggc tcaattaatc tttgtaaata   2160
tgagcgtttt tacgttcaca ttgcctttttt tttatgtat ttaccttgca tttttgtgct   2220
aaaaggcgtc acgttttttt ccgccgcagc cgcccggaaa tgaaaagtat gacccccgct   2280
agaccaaaaa tacttttgtg ttattggagg atcgcaatcc ctactagtta gagattacta   2340
catattccaa caagaccttc gcaggaaagt atacctaaac taattaaaga atctccgaa    2400
gttcgcattt cattgaacgg ctcaattaat ctttgtaaat atgagcgttt ttacgttcac   2460
attgcctttt tttttatgta tttaccttgc attttgtgc taaaaggcgt cacgtttttt   2520
tccgccgcag ccgcccggaa atgaaaagta tgacccccgc tagaccaaaa atactttgt   2580
gttattggag gatcgcaatc cctgtcgact ttcttataat ttttatcaat taccaaatat   2640
atataaatgc aattaattga ttgttcctgt cacataattt ttttgtttg ttacctttat    2700
tctttatcca tttaatttat ttcttgtatc tttctttct atttctcttt tctgtttaat   2760
ctcaccgtac acatatat ccatatatca atacaaataa aaatcattta aaagaattca   2820
acaaaatgtc ttctatgcca aatcatcaaa aagttgtttt ggttggtgat ggtgctgttg   2880
gttcttctta tgcttttgct atggctcaac aaggtattgc tgaagaattt gttattgttg   2940
atgttgttaa agatagaact aaaggtgatg ctttggattt ggaagatgct caagctttta   3000
ctgctccaaa aaaatttat tctggtgaat attctgattg taaagatgct gatttggttg   3060
ttattactgc tggtgctcca caaaaaccag gtgaatctag attggatttg gttaataaaa   3120
```

```
atttgaatat tttgtcttct attgttaaac cagttgttga ttctggtttt gatggtattt    3180
ttttggttgc tgctaatcca gttgatattt tgacttatgc tacttggaaa ttttctggtt    3240
ttccaaaaga aagagttatt ggttctggta cttctttgga ttcttctaga ttgagagttg    3300
ctttgggtaa acaatttaat gttgatccaa gatctgttga tgcttatatt atgggtgaac    3360
atggtgattc tgaatttgct gcttattcta ctgctactat tggtactaga ccagttagag    3420
atgttgctaa agaacaaggt gtttctgatg atgatttggc taaattggaa gatggtgtta    3480
gaaataaagc ttatgatatt attaatttga aaggtgctac ttttttatggt attggtactg    3540 ctttgatgag aatttctaaa gctatttttga gagatgaaaa tgctgttttg ccagttggtg    3600
cttatatgga tggtcaatat ggtttgaatg atatttatat tggtactcca gctattattg    3660
gtggtactgg tttgaaacaa attattgaat ctccattgtc tgctgatgaa ttgaaaaaaa    3720
tgcaagattc tgctgctact ttgaaaaaag tttttgaatga tggtttggct gaattggaaa    3780
ataaataact cgagtcatgt aattagttat gtcacgctta cattcacgcc ctccccccac    3840
atccgctcta accgaaaagg aaggagttag acaacctgaa gtctaggtcc ctatttattt    3900
ttttatagtt atgttagtat taagaacgtt atttatattt caaattttc ttttttttct    3960 gtacagacgc gtgtacgcat gtaacattat actgaaaacc ttgcttgaga aggttttggg    4020
acgctcgaag gctttaattt gcgcggccgc cagcttttgt tccctttagt gagggttaat    4080
tgcgcgcttg gcgtaatcat ggtcatagct gtttcctgtg tgaaattgtt atccgctcac    4140
aattccacac aacataggag ccggaagcat aaagtgtaaa gcctggggtg cctaatgagt    4200
gaggtaactc acattaattg cgttgcgctc actgcccgct ttccagtcgg gaaacctgtc    4260
gtgccagctg cattaatgaa tcggccaacg cgcggggaga ggcggtttgc gtattgggcg    4320
ctcttccgct tcctcgctca ctgactcgct gcgctcggtc gttcggctgc ggcgagcggt    4380
atcagctcac tcaaaggcgg taatacggtt atccacagaa tcaggggata acgcaggaaa    4440
gaacatgtga gcaaaaggcc agcaaaaggc caggaaccgt aaaaaggccg cgttgctggc    4500
gtttttccat aggctccgcc cccctgacga gcatcacaaa aatcgacgct caagtcagag    4560
gtggcgaaac ccgacaggac tataaagata ccaggcgttt ccccctggaa gctccctcgt    4620
gcgctctcct gttccgaccc tgccgcttac cggatacctg tccgcctttc tcccttcggg    4680
aagcgtggcg ctttctcata gctcacgctg taggtatctc agttcggtgt aggtcgttcg    4740
ctccaagctg ggctgtgtgc acgaaccccc cgttcagccc gaccgctgcg ccttatccgg    4800
taactatcgt cttgagtcca acccggtaag acacgactta tcgccactgg cagcagccac    4860
tggtaacagg attagcagag cgaggtatgt aggcggtgct acagagttct tgaagtggtg    4920
gcctaactac ggctacacta aggacagt atttggtatc tgcgctctgc tgaagccagt    4980
taccttcgga aaaagagttg gtagctcttg atccggcaaa caaaccaccg ctggtagcgg    5040
tggttttttt gtttgcaagc agcagattac gcgcagaaaa aaaggatctc aagaagatcc    5100
tttgatcttt tctacggggt ctgacgctca gtggaacgaa aactcacgtt aagggatttt    5160
ggtcatgaga ttatcaaaaa ggatcttcac ctagatcctt ttaaattaaa aatgaagttt    5220
taaatcaatc taaagtatat atgagtaaac ttggtctgac agttaccaat gcttaatcag    5280
tgaggcacct atctcagcga tctgtctatt tcgttcatcc atagttgcct gactccccgt    5340
cgtgtagata actacgatac gggagggctt accatctggc cccagtgctg caatgatacc    5400
gcgagaccca cgctcaccgg ctccagattt atcagcaata aaccagccag ccggaagggc    5460
```

```
cgagcgcaga agtggtcctg caactttatc cgcctccatc cagtctatta attgttgccg    5520
ggaagctaga gtaagtagtt cgccagttaa tagtttgcgc aacgttgttg ccattgctac    5580
aggcatcgtg gtgtcacgct cgtcgtttgg tatggcttca ttcagctccg gttcccaacg    5640
atcaaggcga gttacatgat cccccatgtt gtgcaaaaaa gcggttagct ccttcggtcc    5700
tccgatcgtt gtcagaagta agttggccgc agtgttatca ctcatggtta tggcagcact    5760
gcataattct cttactgtca tgccatccgt aagatgcttt tctgtgactg gtgagtactc    5820
aaccaagtca ttctgagaat agtgtatgcg gcgaccgagt tgctcttgcc cggcgtcaat    5880
acgggataat accgcgccac atagcagaac tttaaaagtg ctcatcattg gaaaacgttc    5940
ttcggggcga aaactctcaa ggatcttacc gctgttgaga tccagttcga tgtaacccac    6000
tcgtgcaccc aactgatctt cagcatcttt tactttcacc agcgtttctg ggtgagcaaa    6060
aacaggaagg caaaatgccg caaaaaaggg aataagggcg acacggaaat gttgaatact    6120
catactcttc ctttttcaat attattgaag catttatcag ggttattgtc tcatgagcgg    6180
atacatattt gaatgtattt agaaaaataa acaataggg gttccgcgca catttccccg    6240
aaaagtgcca cctgtcaaca tctttggata atatcagaat gagaaagaac agatacgcag    6300
tacgttttt ggtgagctct ttgcacttct ttagttcttt ccatcaatat cagtttttta    6360
aactttagg actaaaagtg atgtttaact tcaaaatgtt taaaattttg ttcttcccga    6420
cgttcattaa gaatactaat acactttaat aattatttta atattttgtt ctaaataatg    6480
acttttaatt aaaaaagata aaatataaaa acatcataat aactcaccag aggttaagaa    6540
caaaaaaaca aattagatat ctgctaatcc aatatagtta aatcaatctt ccttggtat    6600
aatgggtata ttacatatat ttcaaggacc gacactccta ccaaatatct aaaatttacc    6660
atattaacat aacatgtata taaacgtcaa atcataatca gcactataag aaaccattat    6720
tatcatgaca ttaacctata aaaataggcg tatcacgagg cccttcgtc                6770
```

<210> SEQ ID NO 10
<211> LENGTH: 7245
<212> TYPE: DNA
<213> ORGANISM: Artificial Sequence
<220> FEATURE:
<223> OTHER INFORMATION: Plasmid 3CIT-pTEF1-LpLDH-CYC1t

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataccac agcttttcaa ttcaattcat cattttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
```

```
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccgta tgcggtgtga ataccgcac    1320 agatgcgtaa ggagaaaata ccgcatcagg aaattgtaaa cgttaatatt ttgttaaaat   1380
tcgcgttaaa ttttgttaa atcagctcat ttttaacca ataggccgaa atcggcaaaa      1440
tcccttataa atcaaaagaa tagaccgaga tagggttgag tgttgttcca gtttggaaca    1500
agagtccact attaagaac gtggactcca acgtcaaagg gcgaaaaacc gtctatcagg     1560 gcgatgccc actacgtgaa ccatcaccct aatcaagttt tttggggtcg aggtgccgta     1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact ataggcgaa ttgggtacca cgtccgaggg ggcccgcaga aacctctcga    2040
gactagttag agattactac atattccaac aagaccttcg caggaaagta tacctaaact    2100
aattaaagaa atctccgaag ttcgcatttc attgaacggc tcaattaatc tttgtaaata    2160
tgagcgtttt tacgttcaca ttgccttttt ttttatgtat ttaccttgca ttttgtgct    2220 aaaaggcgtc acgttttttt ccgccgcagc cgcccggaaa tgaaaagtat gaccccgct     2280 agaccaaaaa tacttttgtg ttattggagg atcgcaatcc ctactagtta gagattacta    2340
catattccaa caagaccttc gcaggaaagt atacctaaac taattaaaga atctccgaa     2400 gttcgcattt cattgaacgg ctcaattaat cttttgtaaat atgagcgttt ttacgttcac    2460
attgcctttt tttttatgta tttaccttgc attttttgtgc taaaaggcgt cacgttttt    2520 tccgccgcag ccgcccggaa atgaaaagta tgaccccgc tagaccaaaa atacttttgt     2580
gttattggag gatcgcaatc cctgtcgact agagattact acatattcca acaagacctt    2640
cgcaggaaag tatacctaaa ctaattaaag aaatctccga agttcgcatt tcattgaacg    2700
gctcaattaa tcttttgtaaa tatgagcgtt tttacgttca cattgccttt tttttttatgt   2760 atttaccttg cattttttgtg ctaaaaggcg tcacgttttt ttccgccgca gccgcccgga   2820
aatgaaaagt atgaccccg ctagaccaaa aatacttttg tgttattgga ggatcgcaat     2880
ccctgagctc atagcttcaa aatgtttcta ctccttttt actcttccag attttctcgg     2940
actccgcgca tcgccgtacc acttcaaaac acccaagcac agcatactaa atttcccctc    3000
tttcttcctc tagggtgtcg ttaattaccc gtactaaagg tttggaaaag aaaaagagag    3060
ccgcctcgtt tcttttttctt cgtcgaaaaa ggcaataaaa atttttatca cgtttctttt   3120
```

```
tcttgaaaat ttttttttg atttttttct ctttcgatga cctcccattg atatttaagt    3180
taataaacgg tcttcaattt ctcaagtttc agtttcattt ttcttgttct attacaactt    3240
ttttacttc ttgctcatta gaaagaaagc atagcaatct aatctaagga attcaacaaa    3300
atgtcttcta tgccaaatca tcaaaaagtt gttttggttg gtgatggtgc tgttggttct    3360
tcttatgctt ttgctatggc tcaacaaggt attgctgaag aatttgttat tgttgatgtt    3420
gttaaagata gaactaaagg tgatgctttg gatttggaag atgctcaagc ttttactgct    3480
ccaaaaaaaa tttattctgg tgaatattct gattgtaaag atgctgattt ggttgttatt    3540
actgctggtg ctccacaaaa accaggtgaa tctagattgg atttggttaa taaaaatttg    3600
aatatttgt cttctattgt taaaccagtt gttgattctg gttttgatgg tatttttttg    3660
gttgctgcta atccagttga tattttgact tatgctactt ggaaattttc tggttttcca    3720
aaagaaagag ttattggttc tggtacttct ttggattctt ctagattgag agttgctttg    3780
ggtaaacaat ttaatgttga tccaagatct gttgatgctt atattatggg tgaacatggt    3840
gattctgaat ttgctgctta ttctactgct actattggta ctagaccagt tagagatgtt    3900
gctaaagaac aaggtgtttc tgatgatgat ttggctaaat tggaagatgg tgttagaaat    3960
aaagcttatg atattattaa tttgaaaggt gctacttttt atggtattgg tactgctttg    4020
atgagaattt ctaaagctat tttgagagat gaaaatgctg ttttgccagt tggtgcttat    4080
atggatggtc aatatggttt gaatgatatt tatattggta ctccagctat tattggtggt    4140
actggttttga aacaaattat tgaatctcca ttgtctgctg atgaattgaa aaaaatgcaa    4200
gattctgctg ctactttgaa aaaagttttg aatgatggtt ggctgaatt ggaaaataaa    4260
taactcgagt catgtaatta gttatgtcac gcttacattc acgccctccc cccacatccg    4320
ctctaaccga aaaggaagga gttagacaac ctgaagtcta ggtccctatt tatttttta    4380
tagttatgtt agtattaaga acgttattta tatttcaaat tttctttt tttctgtaca    4440
gacgcgtgta cgcatgtaac attatactga aaaccttgct tgagaaggtt ttgggacgct    4500
cgaaggcttt aatttgcgcg gcgccagct ttgttccct ttagtgaggg ttaattgcgc    4560
gcttggcgta atcatggtca tagctgtttc ctgtgtgaaa ttgttatccg ctcacaattc    4620
cacacaacat aggagccgga agcataaagt gtaaagcctg gggtgcctaa tgagtgaggt    4680
aactcacatt aattgcgttg cgctcactgc ccgctttcca gtcgggaaac ctgtcgtgcc    4740
agctgcatta atgaatcggc caacgcgcgg ggagaggcgg tttgcgtatt gggcgctctt    4800
ccgcttcctc gctcactgac tcgctgcgct cggtcgttcg gctgcggcga gcggtatcag    4860
ctcactcaaa ggcggtaata cggttatcca cagaatcagg ggataacgca ggaaagaaca    4920
tgtgagcaaa aggccagcaa aaggccagga accgtaaaaa ggccgcgttg ctggcgtttt    4980
tccataggct ccgcccccct gacgagcatc acaaaaatcg acgctcaagt cagaggtggc    5040
gaaacccgac aggactataa agataccagg cgtttccccc tggaagctcc ctcgtgcgct    5100
ctcctgttcc gaccctgccg cttaccggat acctgtccgc ctttctccct tcgggaagcg    5160
tggcgctttc tcatagctca cgctgtaggt atctcagttc ggtgtaggtc gttcgctcca    5220
agctgggctg tgtgcacgaa ccccccgttc agcccgaccg ctgcgcctta tccggtaact    5280
atcgtcttga gtccaacccg gtaagacacg acttatcgcc actggcagca gccactggta    5340
acaggattag cagagcgagg tatgtaggcg gtgctacaga gttcttgaag tggtggccta    5400
actacgctca cactagaagg acagtatttg gtatctgcgc tctgctgaag ccagttacct    5460
tcggaaaaag agttggtagc tcttgatccg gcaaacaaac caccgctggt agcggtggtt    5520
```

```
ttttttgtttg caagcagcag attacgcgca gaaaaaaagg atctcaagaa gatcctttga      5580
tcttttctac ggggtctgac gctcagtgga acgaaaactc acgttaaggg attttggtca      5640
tgagattatc aaaaaggatc ttcacctaga tccttttaaa ttaaaaatga agttttaaat      5700
caatctaaag tatatatgag taaacttggt ctgacagtta ccaatgctta atcagtgagg      5760
cacctatctc agcgatctgt ctatttcgtt catccatagt tgcctgactc cccgtcgtgt      5820
agataactac gatacgggag ggcttaccat ctggccccag tgctgcaatg ataccgcgag      5880
acccacgctc accggctcca gatttatcag caataaacca gccagccgga agggccgagc      5940
gcagaagtgg tcctgcaact ttatccgcct ccatccagtc tattaattgt tgccgggaag      6000
ctagagtaag tagttcgcca gttaatagtt tgcgcaacgt tgttgccatt gctacaggca      6060
tcgtggtgtc acgctcgtcg tttggtatgg cttcattcag ctccggttcc caacgatcaa      6120
ggcgagttac atgatccccc atgttgtgca aaaaagcggt tagctccttc ggtcctccga      6180
tcgttgtcag aagtaagttg gccgcagtgt tatcactcat ggttatggca gcactgcata      6240
attctcttac tgtcatgcca tccgtaagat gcttttctgt gactggtgag tactcaacca      6300
agtcattctg agaatagtgt atgcggcgac cgagttgctc ttgcccggcg tcaatacggg      6360
ataataccgc gccacatagc agaactttaa aagtgctcat cattggaaaa cgttcttcgg      6420
ggcgaaaact ctcaaggatc ttaccgctgt tgagatccag ttcgatgtaa cccactcgtg      6480
cacccaactg atcttcagca tcttttactt tcaccagcgt ttctgggtga gcaaaaacag      6540
gaaggcaaaa tgccgcaaaa aagggaataa gggcgacacg gaaatgttga atactcatac      6600
tcttcctttt tcaatattat tgaagcattt atcagggtta ttgtctcatg agcggataca      6660
tatttgaatg tatttagaaa aataaacaaa taggggttcc gcgcacattt ccccgaaaag      6720
tgccacctgt caacatcttt ggataatatc agaatgagaa agaacagata cgcagtacgt      6780
tttttggtga gctctttgca cttctttagt tctttccatc aatatcagtt ttttaaactt      6840
ttaggactaa aagtgatgtt taacttcaaa atgtttaaaa ttttgttctt cccgacgttc      6900
attaagaata ctaatacact ttaataatta ttttaatatt ttgttctaaa taatgacttt      6960
taattaaaaa agataaaata taaaaacatc ataataactc accagaggtt aagaacaaaa      7020
aaacaaatta gatatctgct aatccaatat agttaaatca atctttcctt ggtataatgg      7080
gtatattaca tatatttcaa ggaccgacac tcctaccaaa tatctaaaat ttaccatatt      7140
aacataacat gtatataaac gtcaaatcat aatcagcact ataagaaacc attattatca      7200
tgacattaac ctataaaaat aggcgtatca cgaggccctt tcgtc                     7245
```

<210> SEQ ID NO 11
<211> LENGTH: 1047
<212> TYPE: DNA
<213> ORGANISM: Artificial Sequence
<220> FEATURE:
<223> OTHER INFORMATION: ADH gene(g4423) allele1_ORF

<400> SEQUENCE: 11

```
atgtctattc caactactca aaagggtgtt atcttctacg aatctagagg taagctagaa        60
tacaaggaca ttccagtccc aactccaaag gctaacgaat tattaatcaa cgttaagtac       120
tctggtgttt gtcacactga tttacacgct tggcacggtg actggccatt gccagttaag       180
ctacctttag tcggtggtca cgaaggtgcc ggtgttgtcg tcgccattgg tgaatccgtt       240
aagggctgga gatcggtga ttacgccggt attaaatggt taaacggttc ttgtatgaac       300
```

```
tgtgaatact gtgaattagg taacgaatct aactgtccag aagctgattt atctggttac    360
actcacgatg gttcttttcca acaatacgct accgctgatg ctatccaagc tgctaagatc   420
ccagccggta ccgatctagc cgaagttgct ccaatcttat gtgctggtgt taccgtctac    480
aaggctctaa agtccgctaa cctaagagct ggtgaatggt gtgctatctc cggtgctgct    540
ggtggtctag gttctctagc tgtccaatac gctaaggcta tgggttacag agtcgtcggt    600
attgacggtg gtgaagaaaa ggaaaagcta ttcaagtcta ttggtggtga agttttcgtc    660
gatttcacta aggaaaagga tatcattggt actattgtca aggccactaa cggtggtgct    720
cacggtgtta tcaacgtctc cgtctctgaa gccgctatcg aagcttctac caagtacgtt    780
agagctaacg gtacctccgt tttagtcggt atgccagctg gtgccgtctg tagatccgat    840
gtctttgacc acgtcgtcaa gtccatctct attgtcggtt cttacgtcgg taacagagct    900
gataccagag aagctctaga cttcttcgcc agaggtttag tcaagtctcc aatcaagatt    960
gctccattat ctgacttacc agaaattttc gaaagatgg aaaagggtca aatcgttggt    1020
agatacgttt tgacacttc taactaa                                         1047
```

```
<210> SEQ ID NO 12
<211> LENGTH: 1047
<212> TYPE: DNA
<213> ORGANISM: Artificial Sequence
<220> FEATURE:
<223> OTHER INFORMATION: ADH gene(g4423) allele2_ORF

<400> SEQUENCE: 12
atgtctattc caactactca aaagggtgtt atcttctacg aatctagagg taagctagaa     60
tacaaggaca ttccagtccc aactccaaag gctaacgaat tattaatcaa cgttaagtac    120
tctggtgttt gtcacactga tttacacgct tggcacggtg actggccatt gccagttaag    180
ctacctttag tcggtggtca cgaaggtgcc ggtgttgtcg tcgccatggg tgaatccgtt    240
aagggctgga gatcggtga ttcgccggt attaaatggt taaacggttc ttgtatgaac    300
tgtgaatact gtgaattagg taacgaatct aactgtccag aagctgattt atctggttac    360
actcacgatg gttcttttcca acaatacgct accgctgatg ctatccaagc tgctaagatc   420
ccagccggta ccgatctagc cgaagttgcc ccaatcttat gtgctggtgt taccgtctac    480
aaggctctaa agtccgctaa cctaagagct ggtgaatggt gtgctatctc cggtgctgct    540
ggtggtctag gttctctagc tgtccaatac gctaaggcta tgggttacag agtcgtcggt    600
attgacggtg gtgatgaaaa ggaaaagcta ttcaagtcca ttggtggtga agttttcgtc    660
gatttcacta aggaaaagga tatcattggt actattgtta aggccactaa cggtggtgct    720
cacggtgtta tcaacgtctc cgtctctgaa gccgctatcg aagcttctac caagtacgtt    780
agagctaacg gtacctccgt tttagtcggt atgccagctg gtgctgtctg tagatccgat    840
gtctttgacc acgtcgtcaa gtccatctct attgtcggtt cttacgtcgg taacagagct    900
gataccagag aagctctaga cttcttcgcc agaggtttag tcaagtctcc aatcaagatt    960
gctccattat ctgacttacc agaaattttc gaaagatgg aaaagggtca aatcattggt    1020
agatacgttt tgacacttc taactaa                                         1047
```

```
<210> SEQ ID NO 13
<211> LENGTH: 1074
<212> TYPE: DNA
<213> ORGANISM: Artificial Sequence
<220> FEATURE:
<223> OTHER INFORMATION: MCR gene
```

<400> SEQUENCE: 13

```
atgagaagaa ctttgaaggc tgccatttta ggtgctacag gtttagtcgg tattgaatac      60
gtcagaatgt tatcacaaca cccatatatt aaacctgctt atttggctgg taaaggttct     120
gttggtaaag cttactcaga agttgtcaga tggcaaacag ttggtcaagt cccaaaggaa     180
gtagccgata tgccagtttt gcctaccgac gtcaatgaaa tcaaaaaggc tggtgtagat     240
attgttttct ctccattacc tcaaggtgct gcaggtccag ttgaagaaga atttgcaaaa     300
gccggtttcc ctgtcatttc taattcacca gatcatagat tcgatccaga cgtacctttg     360
atgtacctg aagttaacgg tcacactgca tccttaattg atgaacaaaa gaaaagaaga     420
gactggagtg gttttattgt tactacacca ttgtgtacag cacaaggtat tgccatacca     480
ttagctccta tctatagaga tttcagagtt gattctgtat tcataaccac tatgcaatcc     540
ttgagtggtg aaggttatcc tggtgttgct tcattggatg tagttgacaa catcaaggtt     600
ttgggtgacg cttacgacgc taaaactgtt aaggaagtca caagaatttt atctgaagtt     660
aagagaaacg tcccaggtac tatggatgaa ttgactttat cagcaacaac ccatagaata     720
gccaccattc atggtcacta cgaagtaatg tacgttactt ttaaagaaga tgtcaaggta     780
gaaaaggtta aggaaacttt ggctaacttc aaaggtgaac ctcaagatat gaagttacca     840
acagcacctt ccagaccaat cttgattacc gaattagata cagaccaca accttacttc     900
gatagatggg caggtgacgt tccaggtatg tccgtcgtag ttggtagatt aaagcaagtt     960
aacaacagaa ctgttagatt ggtttctttg atccataaca cagtcagagg tgccgctggt    1020
ggtggtattt tggtagccga atatttgatc gaaaagggtt acatccctaa gtga          1074
```

<210> SEQ ID NO 14
<211> LENGTH: 988
<212> TYPE: DNA
<213> ORGANISM: Artificial Sequence
<220> FEATURE:
<223> OTHER INFORMATION: ADH gene(g4423) 5UTR allele1

<400> SEQUENCE: 14

```
gttaactcag ttttctctct ttccctccac cccacgttac tctgcgaaca aaaatacgca      60
cagaatgaac atctgattga ttaatattta tatattactt agtggcaccc ctacaaacaa     120
accaattttg aatatttctc accatcatga tatttattta gggcaagaat tcatgtaca     180
tacgtgcgtg tactgcatag ttttgttata tgtaaataac cagcaatata tcaccaatga     240
taaatgctca gtaattttatt tggaaccaaa atagtttcag taatcaaata atacaataac     300
taacaagtgc tgattataca acagctgtta acaacacaaa cacgctctct tctattctct     360
tccctgcttg ttcgtgtggt atattcccga atttgcaatt tagaaattat attttttaaa     420
agaattgttc tccatttttct ggtagtcgta agtggcaaat tggatcataa gacacaatct     480
tgttagttcg actgctaaca ccagacaaga ccgaacgaaa acagaaaaaa aagataaattt     540
tgttattctg ttcaattctc tctctctttt taaggtatct ttacattaca ttacatatcc     600
caaattacaa caagagcaag aaatgaagca caacaacacg ccatctttcg tgattatttt     660
atcatttcta tatcgtaact aaattaacaa atgctatgtt tcttaatttt taatgataaa     720
tctaactgct accttaattt ctcatggaaa gtggcaaata cagaaattat atattcttat     780
tcatttttctt ataattttta tcaattacca aatatatata aatgcaatta attgattgtt     840
cctgtcacat aattttttttt gtttgttacc tttattcttt atccatttag tttagttctt     900
```

```
atatctttct tttctatttc tcttttttcgt ttaatctcac cgtacacata tatatccata    960
tatcaataca aataaaaatc atttaaaa                                        988

<210> SEQ ID NO 15
<211> LENGTH: 961
<212> TYPE: DNA
<213> ORGANISM: Artificial Sequence
<220> FEATURE:
<223> OTHER INFORMATION: ADH gene(g4423) 5UTR allele2

<400> SEQUENCE: 15
gttaactcag ttttctctct ttccctccac cccacgttac tctgcgaaca aaaaatacgc     60
acagaatgaa catctgattg attaatattt atatattact cagtggcacc cctacaaaca    120
aaccaatttt gaatattgtt caccatcatg atatttattt agggcaagaa tttcatgtac    180
atacgtgcgt gtactgcata gttttgttat atgaaaataa ccagcaatat atcaccaatg    240
aataaattct caataattta tttggaacca aataatgcaa taactagcaa actaagtggt    300
gattatacaa cagctgttaa caacacaaac atacgctctc ttctattatc tcttccctgc    360
ttgttcgtgt ggtatattca cgaatttgca atttagaaat tatattttt aaaagaattg     420 ttctccattt tctggtagtc gtaagtggca aattggatca taagacacaa tcttgttagt    480
tcgactgcta acaccagaca acaccgaacg aaaacaagaa aaaataatta ttctctctct    540
ttttaaggta tcttacatta catatcccaa attacaacaa gagcaagaaa tgaggcacaa    600
caacacacca tcatctttcg tgattatttt tatcatttct atcatgtaat taaattaaca    660
aatgttaagt ttattaattt ttaatgataa atctagttgc taccttaatt tctcatggaa    720
agtggcaaat actgaaatta tttaattcta ctttcatttt cttataattt ttatcaatta    780
ccaaatatat ataaatgcaa ttaattgatt gttcctgtca cataattttt tttgtttgtt    840 accttttattc tttatccatt taatttattt cttgtatctt tcttttctat ttctcttttc    900
tgtttaatct caccgtacac atatatatcc atatatcaat acaaataaaa atcatttaaa    960
a                                                                    961

<210> SEQ ID NO 16
<211> LENGTH: 256
<212> TYPE: DNA
<213> ORGANISM: Artificial Sequence
<220> FEATURE:
<223> OTHER INFORMATION: ADH gene(g4423) 3UTR allele1

<400> SEQUENCE: 16
taagtcattt aatttattct tttagaatat atttattttg tctttatttt tgaaatgtta     60
atagtctttt ttttttactt tgaacaaaaa aaagtaaaat taaaacttat cttatatacg    120
cttttaaaca ttaaactcgt taacgaatta tataatgatt ttatcgaact actttatgtt    180
tttttaatag aataatcttc tttattaata taacttacta cttcttaatc ttgttgtcct    240
ccattcgaaa ctcgag                                                    256

<210> SEQ ID NO 17
<211> LENGTH: 255
<212> TYPE: DNA
<213> ORGANISM: Artificial Sequence
<220> FEATURE:
<223> OTHER INFORMATION: ADH gene(g4423) 3UTR allele2

<400> SEQUENCE: 17
taagtcattt aatttattct tttagaatat atttattttg tctttatttt tgaaatgtta     60
```

-continued

```
atagtcttt  tttactttg   aaaaaaaaaa  aaagtaaaat  taaacttatc  ttatatacgc      120
ttttaaacat  taaactcgtt  aacgaattat  ataatgattt  tatcgaacta  ctttatgttt     180
ttttaataga  ataatcttct  ttattaatat  aacttactac  ttcttaatct  tgttgtcctc     240
cattcgaaac  tcgag                                                          255
```

<210> SEQ ID NO 18
<211> LENGTH: 1000
<212> TYPE: DNA
<213> ORGANISM: Artificial Sequence
<220> FEATURE:
<223> OTHER INFORMATION: 18 ADH gene(g4423) 1kb promoter (allele 1)

<400> SEQUENCE: 18

```
gcagcaaccg  cggcttcctc  tagcacgttc  cacgcttttt  atagtggtta  actcagtttt      60
ctctctttcc  ctccacccca  cgttactctg  cgaacaaaaa  tacgcacaga  atgaacatct     120
gattgattaa  tatttatata  ttactcagtg  gcacccctac  aaacaaacca  attttgaata     180
ttgttcacca  tcatgatatt  tatttagggc  aagaatttca  tgtacatacg  tgcgtgtact     240
gcatagtttt  gttatatgaa  ataaccagc   aatatatcac  caatgaataa  attctcaata     300
atttatttgg  aaccaaataa  tgcaataact  agcaaactaa  gtggtgatta  tacaacagct     360
gttaacaaca  caaacatacg  ctctcttcta  ttatctcttc  cctgcttgtt  cgtgtggtat     420
attcacgaat  ttgcaattta  gaattatat   tttttaaaag  aattgttctc  catttctgg      480 tagtcgtaag  tggcaaattg  gatcataaga  cacaatcttg  ttagttcgac  tgctaacacc     540
agacaacacc  gaacgaaaac  aagaaaaaat  aattattctc  tctctttta   aggtatctta     600 cattacatat  cccaaattac  aacaagagca  agaaatgagg  cacaacaaca  caccatcttt     660
cgtgattatt  ttatcatttc  tatcatgtaa  ttaaattaac  aaatgttaag  tttattaatt     720
tttaatgata  aatctagttg  ctaccttaat  ttctcatgga  aagtggcaaa  tactgaaatt     780
atttattctt  attcattttc  ttataatttt  tatcaattac  caaatatata  taaatgcaat     840
taattgattg  ttcctgtcac  ataatttttt  ttgtttgtta  cctttattct  ttatccattt     900
aatttatttc  ttgtatcttt  cttttctatt  tctcttttct  gtttaatctc  accgtacaca     960
tatatatcca  tatatcaata  caaataaaaa  tcatttaaaa                           1000
```

<210> SEQ ID NO 19
<211> LENGTH: 1000
<212> TYPE: DNA
<213> ORGANISM: Artificial Sequence
<220> FEATURE:
<223> OTHER INFORMATION: 18 ADH gene(g4423) 1kb promoter (allele 2)

<400> SEQUENCE: 19

```
gcagcaaccg  cggcttcctc  tagcacgttt  cacgcttttt  agagtggtta  actcagtttt      60
ctctctttcc  ctccacccca  cgttactctg  cgaacaaaaa  tacgcacaga  atgaacatct     120
gattgattaa  tatttatata  ttacttagtg  gcacccctac  aaacaaacca  attttgaata     180
tttctcacca  tcatgatatt  tatttagggc  aagaatttca  tgtacatacg  tgcgtgtact     240
gcatagtttt  gttatatgta  aataaccagc  aatatatcac  caatgaataa  atgctcagta     300
atttatttgg  aaccaaataa  tgcaataact  agcaaactaa  gtgctgatta  tacaacagct     360
gttaacaaca  caaacatacg  ctctcttcta  ttatctcttc  cctgcttgtt  cgtgtggtat     420
attcccgaat  ttgcaattta  gaattatat   tttttaaaag  aattgttctc  catttctgg      480
```

```
tagtcgtaag tggcaaattg gatcataaga cacaatcttg ttagttcgac tgctaacacc      540
agacaagacc gaacgaaaac aagaaaaaat aattattctc tctcttttta aggtatctta      600
cattacatat cccaaattac aacaagagca agaaatgaag cacaacaaca cgccatcttt      660
cgtgattatt ttatcatttc tatatcgtaa ctaaattaac aaatgctatg tttcttaatt      720
tttaatgata aatctaactg ctaccttaat ttctcatgga aagtggcaaa tacagaaatt      780
atatattctt attcattttc ttataatttt tatcaattac caaatatata taaatgcaat      840
taattgattg ttcctgtcac ataattttt ttgtttgtta cctttattct ttatccattt      900
agtttagttc ttatatcttt cttttctatt tctcttttc gtttaatctc accgtacaca      960
tatatatcca tatatcaata caaataaaaa tcatttaaaa                          1000

<210> SEQ ID NO 20
<211> LENGTH: 918
<212> TYPE: DNA
<213> ORGANISM: Artificial Sequence
<220> FEATURE:
<223> OTHER INFORMATION: ald2 5UTR (allele1)

<400> SEQUENCE: 20
agagttacgt gatcagaatg ggaaactgtt accacctcca cctggatttg aattcagcac       60
ttcctttgaa tcgaagctaa caccagagga gataaatatg aattctttac caatggaacc      120
acctaattat tcagataatg aaagtacata tgcatttaaa tttcatccaa gagattcatt      180
atcaagcaac acgagtagaa ccatcccaat tgtaggaagt agtaaaagat tagacaatag      240
gatcctggtc ggaagtagca gcaaccgttt aagaaattcc ccagatgata aagacgacta      300
cgatttcgat gatgacgagg attacgacta cgatgaatat gatatccccg aggatgatga      360
tgacgacaac aacgatgata tccatgatat ccatgatatc cacgatatcg agaccgatga      420
ggacgacgaa gagatcacag atgaaatggc acacatgatc tcccatcagt gatcttatat      480
aaatatacaa gataatatat atatatat atgtaacatc taaagacaga tacccgatcg      540
tcttccttat tcttccaaag gactctgaag ttggcccgaa attagcaccg aaatcgggaa      600
caaccaacac ggcgacaccc gtggagcgac tgcgcgaaac aggcaggagt ggcctgacag      660
aacaatgtgc catctctgcg tatcggagtc gtcgttgata acggggggg gggcagacag      720 aaagagaaaa gggggcgaca tcaattccgg cggtggaggg gggagtcat cccatgtttt      780 gtcattatta ttatataagg tagatatgac ggataaagat ttgttgggta tgcttttttg      840
aactaactta tatatatatt atatattaca gcacggttca atataacagg gactgttgag      900
tgagataaca ttaaattc                                                   918

<210> SEQ ID NO 21
<211> LENGTH: 909
<212> TYPE: DNA
<213> ORGANISM: Artificial Sequence
<220> FEATURE:
<223> OTHER INFORMATION: ald2 5UTR (allele2)

<400> SEQUENCE: 21
agagttacgt gatcagaatg ggaaattatt accacctcca cctggattcg aattcagcac       60
ttcctttgaa tcgaagctaa caccagagga gataaatatg aattctttac caatggaacc      120
acctaattat tcagataatg aaagtacata tgcatttaaa tttcatccaa gagattcatt      180
atcaagcaat acaggtagaa ccatcccaat tgtaggaagt agcaaaagat tagacaatag      240
gatcctggta ggaagtagca gcaaccgttt aaggaattcc ccagatgata aagacgacta      300
```

-continued

```
cgatttcgat gatgacgacg attgcgacta cgatgaatat gatatccccg aggatgatga      360
tgacgacaac aacgataata tccatgatat ccacgatatc gagaccgatg aagacgacga      420
agagatcaca gatgaaatgg cacacatgat ctcccatcag tgatcttata taaatataca      480
agataatata tatatatatg taacatctaa agacagatac ccgatcgtct tccttattct      540
tccaaaggac tctgaagttg gcccgaaatt agcaccgaaa tcgggaacaa ccaacacggc      600 gacaccegtg gagcgactgc gcgggaaaca ggagtggcct gacagacagc gacaacaata      660
tgccatttct gcgtatcgga gtcgtcgttg atagcggggg gtgggcagac agaaagagaa      720
aagcgggcga catcaattcc ggcggtggag ggggagtca tcccatgttt tgtcattatt       780
attatataaa gtagatatga ctgataaaga tttgttgggt atgctttttt gaactaactt      840
ataaacatat tatatattac aacacggttc aatataacaa ggactgttga gtgagataac      900
attaaattc                                                             909
```

```
<210> SEQ ID NO 22
<211> LENGTH: 999
<212> TYPE: DNA
<213> ORGANISM: Artificial Sequence
<220> FEATURE:
<223> OTHER INFORMATION: ald2 3UTR (allele1)

<400> SEQUENCE: 22
```

```
tgctggtata cctataaata tttatgtact ttctatatca gtactttact aataatatat       60
atatttttta ttctattgaa tattcctcga tcgatttttt tattatgcgc tgatgacgaa      120
aatgtaaaca aagcgcgaaa acgcgctaat gaaaatatga tatcgatcct aaagtaatgg      180
aatagttata tcaacagcga cacatggagg acttaacagc ctagtcaagt ttcaactttg      240
taagtaataa ggtatagtca ggaatattca cacaagtatg aacagattgg gaagccaaca      300
aagtacaaag agaccatgtg ctgtttgtac gaaacgtaaa gttaaatgtg atagaaagat      360
accttgtgga aactgtatta aaagaggtca agaagcagaa tgtatcaaaa cggtgacaaa      420
cggattttta catgacccaa attctacaaa tgggacagat ttaattctga atatccttcg      480
aatgtggcca agttatgaat attggataac tgacattggt ttgttcaaga caaagatat      540 agattcaact atcagaatcg aaactttaga agatgagcta agagagatca cattttggac      600
cgattattta acaatggaat cttcctttaa attattaaat ttcgcagtgg agaatctggg      660
tcccttatat tttggttgtc tgggtgatat cagtgaatta tttgtacaac tagagaatta      720
ctggactaga agaaatcaat tcaaagaaaa tccaagggaa accacgttca ctttagatga      780
taattactgg aattcagtac tatgggcaat ttttacaatg gccatgtact atataccgtt      840
agaaaattta tctgatggat tcgaattaca gtctatctgc gaacaattaa atatagatga      900
gaatcaacat tggtctgaat caattcaatt gacagttgta caaggtttta caaaatgttg      960
tatgaaccat ttaaacagag caaaatataa cgagaatcc                            999
```

```
<210> SEQ ID NO 23
<211> LENGTH: 1001
<212> TYPE: DNA
<213> ORGANISM: Artificial Sequence
<220> FEATURE:
<223> OTHER INFORMATION: ald2 3UTR (allele2)

<400> SEQUENCE: 23
```

```
tgctggtata cctataaata tttatgtact ttctatacca gtactttact aataatatat       60
```

| | |
|---|---|
| atatgtatat cttattttat ttaaaattct ttaatcgatt ttattatgcg ttgacgacga | 120 |
| aaatgtaaac aaagcgcgaa aacgcgataa tgaaaatatg agatcgatcc taaattaatg | 180 |
| gactagttat atcaacactg acacatggag gacataataa cttagaaaag tttcaacttt | 240 |
| gtaagtagca aagaatagcc aggaattttt cagacaaata tgaatagact gcgtagtcaa | 300 |
| caaagtacaa agagaccatg tgctgtttgt acgaaacgta aagttaaatg tgatagaaag | 360 |
| ataccttgtg gaaactgtat taaaagaggc caagaagctg aatgtatcaa acggtgaca | 420 |
| aatgggtttt tacatgaccc acattctaca aacggaacag attcaattct taatatcctt | 480 |
| cgaatgtggc caagttatga atattggata actgatattg gtttattcaa gacaaaagat | 540 |
| atagattcaa ctatcagaat cgaaactcta gaagatgaac taagagagat cactttttgg | 600 |
| accgattatt taacaatgga atcttccttt aagctattaa attttgcagt ggagaaccta | 660 |
| ggccccttat attttggttg tctaggtgat atcagtgaat tatttgtaca gctagagaat | 720 |
| tactggacta agagaaatca attcaaagaa aatccaaggg aaaccacgtt cactttagac | 780 |
| gataattact ggaattcagt actatgggca attttcacaa tggccatcta ctatataccg | 840 |
| ttagaaaatt tatctgatga attcgaatta cagtctatct gtgaacaatt aaatatagat | 900 |
| gagaatcaac attggtctga atcaattcaa ttgacagttg tgcaaggttt tacaaaatgt | 960 |
| tgtatggatc atttgaacag agcaaaatat aacgagaatc c | 1001 |

<210> SEQ ID NO 24
<211> LENGTH: 1690
<212> TYPE: DNA
<213> ORGANISM: Artificial Sequence
<220> FEATURE:
<223> OTHER INFORMATION: PDC1 gene (g3002-1) ORF

<400> SEQUENCE: 24

| | |
|---|---|
| atggctgaaa ttcaattagg tcgttactta ttcgaaagat taaagcaagt taaatgtact | 60 |
| accgttttcg gttaccagg tgatttcaac ttggtcttat tagacaagtt atacgaagtc | 120 |
| gaaggtatga gatggtccgg tgacactaac gaattaaacg ctgcttacgc tgctgatggt | 180 |
| tacgctagag ttaagggtat ggccgctatg atcaccactt tcggtgtcgg tgaattatcc | 240 |
| gctttaaacg gtattgccgg ttcttactct gaacacgtcg gtgttttaca cattgtcggt | 300 |
| tgtccatcta cttttactaca agctaagggt ctattattac accacacctt agctgatggt | 360 |
| gacttcgatg tcttccacag aatgtctgct aacatctctt gtactacctc tatgatcact | 420 |
| gacattgcca ctgctccaag tgaaattgac agatgtatca gagctactta catcaaccaa | 480 |
| agaccagtct acttaggttt cccatctgac tactttgaaa agactgttcc agcttctcta | 540 |
| ttacaaactc caattgactt atctctaaag gctaacgatg ctgcttctga agatgaagtt | 600 |
| attgaagaaa tcttaaccat ggttaaggct gctaagaacc caatcatcat tgctgatgct | 660 |
| tgttcttcca gacacaacgt taaggctgaa accaagaagt tagtcgatgt taccaacttc | 720 |
| ccagccttcg ctactcctct aggtaaggcc gtcattgacg aaactcaccc aagattcggt | 780 |
| ggtatctacg ttggttctct atccagacca gctgtcaagg aagccgttga atccgctgat | 840 |
| ttaatcttat ctgtcggtgc tctattatcc gattacaaca ctgcttcttt cacttacggt | 900 |
| tacaacacca gaacattgt tgaattccac tccgaccaca tgaagatcag aaacgctacc | 960 |
| ttcccaggtg tccaaatgaa attcgttcta caaagattac taaaggtcat cggtgaagct | 1020 |
| aacaagggtt acaaggccgt tgctaccca gctaaggctc cagctaacgc tgaagtccca | 1080 |
| gcttctacte cattgaagca agaatggtta tggaacgaag tttccaactt cttccaagaa | 1140 |

```
ggtgatgtta tcatcactga aaccggtact tcttccttcg gtatcaactc ctctgtcttc      1200
ccagccaaca ctattggtat ctctcaagtc ttatggggtt ccattggtta cgctggtggt      1260
gctgttgccg gtgctgcttt cgccgctgaa gaaattgacc cagctaagag agtcattcta      1320
ttcattggtg acggttctct acaattaacc gttcaagaaa tctccaccat tgttagatgg      1380
ggtctaaagc catacttatt cgtcttaaac aacgatggtt acaccattga aagattaatt      1440
cacggtccaa aggctcaata caacgaaatt caaaactggg ataacttaaa gattctacca      1500
accttcggtg ctaaggacta cgaaactcac agagttgcta ccactggtga atggaagaag      1560
ttgatcgctg acaaggcttt caacgttcca tctaagatca gaatgatcga agttatgtta      1620
ccagttatgg atggtccagc tgctttgatc gctcaaggta agctatccga agaaatgaac      1680
gctgctatgt                                                             1690

<210> SEQ ID NO 25
<211> LENGTH: 510
<212> TYPE: DNA
<213> ORGANISM: Artificial Sequence
<220> FEATURE:
<223> OTHER INFORMATION: PDC1 gene (g3002-1) 3UTR Reverse complement

<400> SEQUENCE: 25
ccgaagaact taaagtacca gaagatgtaa gtggagcatc tgttaagaga gatgaaaatt       60
tcttaagaag aaggctgctt cttcgtttaa aagctaaatt acttaatcgc gttaaggagc      120
tgcaaattat caacgatgaa aagaaaccat tggaattgga tgaggaagaa gtatgggcaa      180
ttcaacaaat cgcgaccaga atcttagaaa ggaggtatgg taatgattcg atcgatgatt      240
ctttaaattt ggcaaataag gcaaatgctc tcaattaaat aaataccatg taaataaaat      300
aaatacgtaa caaaatgcat aacatttaat taatatagcc gaaaaataaa tattaaaaga      360
ataaatattc tatttcatta aattttataa agtgatgatg tatgtatgat atgtatgatg      420
aaaaaatgga acgtaaaaaa tattaattaa aagatctttt tcagcttttt tacatagcag      480
cgttcatttc ttcggatagc ttaccttgag                                       510

<210> SEQ ID NO 26
<211> LENGTH: 1094
<212> TYPE: DNA
<213> ORGANISM: Artificial Sequence
<220> FEATURE:
<223> OTHER INFORMATION: PDC1 gene (g3002-1) 5UTR Reverse complement

<400> SEQUENCE: 26
gattggatgt gtataattga ataggatggt tatcttagaa ttgacaagaa atagagaaaa       60
acaattaaca gagaaaattt acaaacggag aattcatttc aaataggaaa acaatctgtt      120
ccttatatat taaaaaaaaa agattaattc agatacgtaa actgaaaaag aaaaaatttt      180
ctcattttga tgatcttagt cctctcaatc tttatgcagt aaaacaacca aactgacatc      240
aaacaaacat caacatcatc aattgttaat atttttattc tatcaactta cttttttctg      300
cccttaaaca atcacaaaga gaaatatttg cccacaaact tcctttgaga gcaaattgtg      360
aatactgtaa attatccgca gaaaatagtt gttttcctgt tgatgattat taaatttgat      420
ctaactctgt ttgactttcg tgaaatttga gaattttttt ttgcttataa tttctctaac      480
aaacaactga tatcctgctg tcaagtaaca aattcttgt taacgattca aaattacaac      540
aaagacgata tcgatgtgaa taattttttca tttacgatct gtgcaacaat tttactggat      600
```

| | |
|---|---|
| caattaaaat aatttttatg ggtggaaatt ttttcgaaat ttaagagtttt tgaataaatt | 660 |
| atgcaaaaaa ttgaaataac cgaaagagat aataaaatac acagagcgaa tttggatgaa | 720 |
| gcgacgagag aaaaaaaaaa taatgtgagt gggatatatg cggaactaaa acagcgcgaa | 780 |
| gaatatacat agttcaagtt tgtttgtttt tttattaaat ctttgagaaa atgaataaat | 840 |
| gcataaattta tgaatttcct gttcaaagag atacgatatt tctggctctt cccgcttttt | 900 |
| tttttactca gatgttctcc agataaataa ataaaaaaaa gaattaatt gtggacgctg | 960 |
| ggtatttttt cgtggaagct aagaagtcag gcacagcaag cgcacatttc tttttttcc | 1020 |
| attatttcat caaagaagaa gcccaaggca cagataaatg aatgctacta ctacacgatt | 1080 |
| tctttggcca tgtt | 1094 |

<210> SEQ ID NO 27
<211> LENGTH: 980
<212> TYPE: DNA
<213> ORGANISM: Artificial Sequence
<220> FEATURE:
<223> OTHER INFORMATION: PDC1 gene (g3002-1) truncated 5UTR

<400> SEQUENCE: 27

| | |
|---|---|
| ttatattctt tcaacgtgca tcagacggtt catacaaaca tggccaaaga aatcgtgtag | 60 |
| tagtagcatt catttatctg tgccttgggc ttcttctttg atgaaataat ggaaaaaaaa | 120 |
| gaaatgtgcg cttgctgtgc ctgacttctt agcttccacg aaaaaatacc cagcgtccac | 180 |
| aattaatttc tttttttttat ttatttatct ggagaacatc tgagtaaaaa aaaaagcggg | 240 |
| aagagccaga aatatcgtat ctctttgaac aggaaattca taaattatgc atttattcat | 300 |
| tttctcaaag atttaataaa aaaacaaaca aacttgaact atgtatattc ttcgcgctgt | 360 |
| tttagttccg catatatccc actcacatta tttttttttt ctctcgtcgc ttcatccaaa | 420 |
| ttcgctctgt gtattttatt atctctttcg gttatttcaa tttttttgcat aatttattca | 480 |
| aaactcttaa atttcgaaaa aatttccacc cataaaaatt atttttaattg atccagtaaa | 540 |
| attgttgcac agatcgtaaa tgaaaaatta ttcacatcga tatcgtcttt gttgtaattt | 600 |
| tgaatcgtta acaagaaatt tgttacttga cagcaggata tcagttgttt gttagagaaa | 660 |
| ttataagcaa aaaaaaattc tcaaatttca cgaaagtcaa acagagttag atcaaattta | 720 |
| ataatcatca acaggaaaac aactattttc tgcggataat ttacgtatt cacaatttgc | 780 |
| ctctcaaagga agtttgtggg caaatatttc tctttgtgat tgtttaaggg cagaaaaaag | 840 |
| taagttgata gaataaaaat attaacaatt gatgatgttg atgtttgttt gatgtcagtt | 900 |
| tggttgtttt actgcataaa gattgagagg actaagatca tcaaaatgag aaaattttt | 960 |
| ctttttcagt ttacgtatct | 980 |

<210> SEQ ID NO 28
<211> LENGTH: 391
<212> TYPE: DNA
<213> ORGANISM: Artificial Sequence
<220> FEATURE:
<223> OTHER INFORMATION: PDC1 gene (g3002-1) truncated 3UTR

<400> SEQUENCE: 28

| | |
|---|---|
| ttatgcattt tgttacgtat ttattttatt tacatggtat ttatttaatt gagagcattt | 60 |
| gccttatttg ccaaatttaa agaatcatcg atcgaatcat taccataccct cctttctaag | 120 |
| attctggtcg cgatttgttg aattgcccat acttcttcct catccaattc caatggtttc | 180 |
| ttttcatcgt tgataatttg cagctcctta acgcgattaa gtaatttagc ttttaaacga | 240 |

```
agaagcagcc ttcttcttaa gaaattttca tctctcttaa cagatgctcc acttacatct    300
tctggtactt taagttcttc ggagatactg tttaataatc tcacagcttc caactgtata    360
tatatctcag aggtgtaatc atgcgcagta a                                   391
```

<210> SEQ ID NO 29
<211> LENGTH: 398
<212> TYPE: DNA
<213> ORGANISM: Artificial Sequence
<220> FEATURE:
<223> OTHER INFORMATION: Saccharomyces cerevisiae TEF1 core-promotor

<400> SEQUENCE: 29

```
atagcttcaa aatgtttcta ctccttttt actcttccag attttctcgg actccgcgca     60
tcgccgtacc acttcaaaac acccaagcac agcatactaa atttcccctc tttcttcctc   120
tagggtgtcg ttaattaccc gtactaaagg tttggaaaag aaaaaagaga ccgcctcgtt   180
tctttttctt cgtcgaaaaa ggcaataaaa attttatca cgtttctttt tcttgaaaat    240 ttttttttg atttttttct ctttcgatga cctcccattg atatttaagt taataaacgg    300
tcttcaattt ctcaagtttc agtttcattt tccttgttct attacaactt tttttacttc   360
ttgctcatta gaaagaaagc atagcaatct aatctaag                           398
```

<210> SEQ ID NO 30
<211> LENGTH: 963
<212> TYPE: DNA
<213> ORGANISM: Artificial Sequence
<220> FEATURE:
<223> OTHER INFORMATION: Bos Taurus LDH

<400> SEQUENCE: 30

```
atgtcttcta tgccaaatca tcaaaaagtt gttttggttg gtgatggtgc tgttggttct    60
tcttatgctt ttgctatggc tcaacaaggt attgctgaag aatttgttat tgttgatgtt   120
gttaaagata gaactaaagg tgatgctttg gatttggaag atgctcaagc ttttactgct   180
ccaaaaaaaa tttattctgg tgaatattct gattgtaaag atgctgattt ggttgttatt   240
actgctggtg ctccacaaaa accaggtgaa tctagattgg atttggttaa taaaaatttg   300
aatattttgt cttctattgt taaaccagtt gttgattctg gttttgatgg tatttttttg   360
gttgctgcta atccagttga tatttttgact tatgctactt ggaaattttc tggttttcca   420
aaagaaagag ttattggttc tggtacttct ttggattctt ctagattgag agttgctttg   480
ggtaaacaat ttaatgttga tccaagatct gttgatgctt atattatggg tgaacatggt   540
gattctgaat tgctgctta ttctactgct actattggta ctagaccagt tagagatgtt   600
gctaaagaac aaggtgtttc tgatgatgat ttggctaaat tggaagatgg tgttagaaat   660
aaagcttatg atattattaa tttgaaaggt gctactttt atggtattgg tactgctttg   720
atgagaattt ctaaagctat tttgagagat gaaaatgctg ttttgccagt tggtgcttat   780
atggatggtc aatatggttt gaatgatatt tatattggta ctccagctat tattggtggt   840
actggtttga aacaaattat tgaatctcca ttgtctgctg atgaattgaa aaaaatgcaa   900
gattctgctg ctactttgaa aaaagttttg aatgatggtt tggctgaatt ggaaaataaa   960
taa                                                                  963
```

<210> SEQ ID NO 31
<211> LENGTH: 711
<212> TYPE: DNA

<213> ORGANISM: Artificial Sequence
<220> FEATURE:
<223> OTHER INFORMATION: mCherry

<400> SEQUENCE: 31

| | | | | | |
|---|---|---|---|---|---|
| atggtgagca | agggcgagga | ggataacatg | gccatcatca | aggagttcat | gcgcttcaag | 60 |
| gtgcacatgg | agggctccgt | gaacggccac | gagttcgaga | tcgagggcga | gggcgagggc | 120 |
| cgccCCtacg | agggcaccca | gaccgccaag | ctgaaggtga | ccaagggtgg | ccccctgccc | 180 |
| ttcgcctggg | acatcctgtc | ccctcagttc | atgtacggct | ccaaggccta | cgtgaagcac | 240 |
| cccgccgaca | tccccgacta | cttgaagctg | tccttcccg | agggcttcaa | gtgggagcgc | 300 |
| gtgatgaact | tcgaggacgg | cggcgtggtg | accgtgaccc | aggactcctc | cctgcaggac | 360 |
| ggcgagttca | tctacaaggt | gaagctgcgc | ggcaccaact | tccCCtccga | cggccccgta | 420 |
| atgcagaaga | agaccatggg | ctgggaggcc | tcctccgagc | ggatgtaccc | cgaggacggc | 480 |
| gccctgaagg | gcgagatcaa | gcagaggctg | aagctgaagg | acggcggcca | ctacgacgct | 540 |
| gaggtcaaga | ccacctacaa | ggccaagaag | cccgtgcagc | tgcccggcgc | ctacaacgtc | 600 |
| aacatcaagt | tggacatcac | ctcccacaac | gaggactaca | ccatcgtgga | acagtacgaa | 660 |
| cgcgccgagg | gccgccactc | caccggcggc | atggacgagc | tgtacaagta | a | 711 |

<210> SEQ ID NO 32
<211> LENGTH: 963
<212> TYPE: DNA
<213> ORGANISM: Artificial Sequence
<220> FEATURE:
<223> OTHER INFORMATION: ldh gene from Lactobacillus plantarum

<400> SEQUENCE: 32

| | | | | | |
|---|---|---|---|---|---|
| atgtcttcta | tgccaaatca | tcaaaaagtt | gttttggttg | gtgatggtgc | tgttggttct | 60 |
| tcttatgctt | ttgctatggc | tcaacaaggt | attgctgaag | aatttgttat | tgttgatgtt | 120 |
| gttaaagata | gaactaaagg | tgatgctttg | gatttggaag | atgctcaagc | ttttactgct | 180 |
| ccaaaaaaaa | tttattctgg | tgaatattct | gattgtaaag | atgctgattt | ggttgttatt | 240 |
| actgctggtg | ctccacaaaa | accaggtgaa | tctagattgg | atttggttaa | taaaaatttg | 300 |
| aatattttgt | cttctattgt | taaaccagtt | gttgattctg | gttttgatgg | tattttttg | 360 |
| gttgctgcta | atccagttga | tattttgact | tatgctactt | ggaaattttc | tggttttcca | 420 |
| aaagaaagag | ttattggttc | tggtacttct | ttggattctt | ctagattgag | agttgctttg | 480 |
| ggtaaacaat | taatgttga | tccaagatct | gttgatgctt | atattatggg | tgaacatggt | 540 |
| gattctgaat | tgctgcctta | ttctactgct | actattggta | ctagaccagt | tagagatgtt | 600 |
| gctaaagaac | aaggtgtttc | tgatgatgat | ttggctaaat | tggaagatgg | tgttagaaat | 660 |
| aaagcttatg | atattattaa | tttgaaaggt | gctactttt | atggtattgg | tactgctttg | 720 |
| atgagaattt | ctaaagctat | tttgagagat | gaaaatgctg | ttttgccagt | tggtgcttat | 780 |
| atggatggtc | aatatggttt | gaatgatatt | tatattggta | ctccagctat | tattggtggt | 840 |
| actggtttga | acaaattat | tgaatctcca | ttgtctgctg | atgaattgaa | aaaaatgcaa | 900 |
| gattctgctg | ctactttgaa | aaaagttttg | aatgatggtt | tggctgaatt | ggaaaataaa | 960 |
| taa | | | | | | 963 |

<210> SEQ ID NO 33
<211> LENGTH: 375
<212> TYPE: DNA
<213> ORGANISM: Artificial Sequence

```
<220> FEATURE:
<223> OTHER INFORMATION: g2947(CYB2 gene) Core-promotor allele 1

<400> SEQUENCE: 33
atatattttg gctgacattg taattagatg agatccacaa tttttctttt gtttgactgt      60
tcgatatgga gaaggtggga tgcactatta ttatattcag aagtttattt gtacagcttg     120
aagaacaaat agtggctaat cctatcctcg gactaaaaaa aattgttcac ttttatccta     180
ctgtaaatct tatgaaaatg atgtaattca tatagttact atattttctt tcttttagaa     240
acttcatgat atatatatat atataaaagg actaatcacc caactctcaa atttattaaa     300
aagaaatatg tttctatcat cttctttct tattatacct tctctaataa taaaaataaa     360
caactttctg taaag                                                     375

<210> SEQ ID NO 34
<211> LENGTH: 375
<212> TYPE: DNA
<213> ORGANISM: Artificial Sequence
<220> FEATURE:
<223> OTHER INFORMATION: g2947(CYB2 gene) Core-promotor allele 2

<400> SEQUENCE: 34
atatattttg gctgacattg taattagatg agatccacaa tttttctttt gtttgactgt      60
tcgatatgga gaaggtggga tgcactatta ttatattcag aagtttattt gtacagttta     120
aagaacaaat agtggctaat cctatcctcg gactaaaaaa aatcgttcac ttctatccta     180
ctgtaaatct tatgaaaatg atgtaattca tatagttact atattttctt tcttttagaa     240
actttatgat atatatatat atataaaagg actaatcacc caactctcaa attcattaaa     300
aagaaatatg tttctatcat cttctttct tattatacct cgtctaataa taaaaccaaa     360
caattttctg taaag                                                     375
```

SYNTHETIC PROMOTER BASED ON GENE FROM ACID-RESISTANT YEAST

CROSS REFERENCE TO RELATED APPLICATIONS

This application claims priority to KR patent application No. 10-2020-0150964, filed Nov. 12, 2020, the contents of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 1, 2021, is named UTF-8PF-B2691_ST25.txt and is 59,505 bytes in size.

TECHNICAL FIELD

The present invention relates to a synthetic promoter capable of controlling the expression of a target gene at various locations in the genome of an acid-resistant strain, and more particularly to a synthetic promoter including a core promoter derived from an acid-resistant strain and an upstream activating sequence (UAS) element serving as an enhancer.

BACKGROUND ART

Bioconversion of various raw materials into chemical materials such as organic acids, alcohols, amines and the like through bio-processing is receiving attention in view of eco-friendliness, carbon dioxide emissions reduction, sustainability, and the supply of new platform chemicals. Through such bioconversion, chemicals, polymers, food, cosmetics, nutraceuticals, and pharmaceutical-related chemical products are supplied.

However, products obtained through bioconversion must typically be subjected to a purification process for removing impurities generated in the production process. Also, when producing an organic acid, fermentation is mostly performed at a neutral pH using a base in order to prevent the growth of a strain from being inhibited by the organic acid that is produced, and acidification is then carried out to separate and purify the organic acid, whereby a large amount of neutralized salt is generated as a byproduct, and the production cost increases due to complicated processing. The high economic burden of this purification process is acting as a factor hindering the entry of fermented products into chemical markets.

With the goal of solving the above problems, in the production of acidic materials such as organic acids, when producing organic acids including lactic acid using microorganisms that are able to grow at low pH and exhibit high fermentation ability, particularly yeast (acid-resistant yeast), which grows well under acidic conditions, there is no need to maintain the medium at a pH of 6-7 using a neutralizer during fermentation, so the fermentation process is simplified, and no downstream purification process for removing the neutralizer is required. Moreover, since yeast synthesizes many components that are necessary for metabolism by itself, it may be cultured in a medium having a lower nutrient level than bacteria, particularly *Lactobacillus*, so many downstream purification processes may be omitted, thereby greatly reducing production costs through simplification of processing and reduced use of additives.

In many cases, however, microorganisms surviving at low pH have a very slow growth rate, so a sufficient amount of cells for material production cannot be obtained, resulting in a low raw-material consumption rate and a low production rate, making it difficult to apply to industrial fermentation processes. Therefore, it is very important to select microorganisms that are able to maintain a high raw-material consumption rate while growing rapidly at a pH lower than the pKa of the product.

Such microorganisms may be selected from a variety of strain libraries through various selection pressures, and examples of selection pressures may include resistance to target product concentration, resistance to raw-material concentration, raw-material consumption rate, pH, growth capacity in minimal media, and the like. The selection of microorganisms may be performed manually, but in the case of screening through automation, strains having excellent properties may be quickly selected from among a larger number of subjects.

The selected microorganisms exhibit excellent properties of withstanding the selection pressures, but in most cases wild-type microorganisms produce other products, rather than the target product. Therefore, in order to impart the selected microorganisms with the ability to produce the target product, research has been conducted with the goals of introducing a gene for obtaining a target product through genetic engineering and of eliminating the ability to produce a product that is originally produced.

In order to impart the selected microorganisms with the ability to produce a target product, a method of introducing a gene for obtaining a target product or increasing the activity of an inherent gene is used, but in general, the activity of the inherent gene and the enzyme produced therefrom is often low, so a strong foreign gene is introduced in most cases. Moreover, in this procedure, it is essential to introduce a promoter capable of increasing expression of foreign DNA.

With regard to usable promoters, when the target microorganism is yeast, a promoter of *Saccharomyces cerevisiae*, which is well-known yeast, may be used, and various genetic engineering techniques developed for *S. cerevisiae* may also be applied. In addition, it is possible to select a strong promoter from among promoters involved in the major carbon flux of the selected microorganism, and it is necessary to preferentially apply a method capable of most effectively expressing the target gene through various techniques. In particular, for the selected acid-resistant yeast, when related genetic engineering studies have not been conducted, it is a common approach to use the promoter of *S. cerevisiae* or to use the inherent promoter of the selected microorganism.

In eukaryotic bacteria, promoters have various regulatory regions including a core promoter region, and the regulatory genes differ between microorganisms. Therefore, the optimal region may be found while confirming the role of the promoter by selecting a sequence having a sufficient length at the 5' end of an ORF. However, additional studies on mechanisms of distal control (enhancer, silencer, etc.) or complex control are needed.

The present inventors selected microorganisms having vastly superior acid resistance and other fermentation properties from 700 kinds of yeast using an automated system, and tried to establish a genetic engineering tool for the corresponding microorganisms, which included the development of a promoter. First, attempts were made to express various genes using the *S. cerevisiae*-derived promoter and the inherent promoter (the upstream 5' UTR of an ORF), and good expression levels were confirmed in some cases, but a sufficiently strong promoter was not discovered. Accordingly, the present inventors proposed a method of using the inherent promoter itself, successfully found, as an appropriate promoter in the genome, a new strong inherent promoter, and confirmed the performance thereof (Korea Patent No. 2,140,596). The corresponding promoter strongly expressed a variety of introduced genes, but due to the characteristics of the inherent promoter, it was impossible to apply to one or more genes due to expression by replacement of the target gene. Since it is often necessary to express various genes in view of the general properties of genetic engineering, the present researchers tried to develop a promoter capable of being used while controlling the expression intensity at various locations in the genome.

As the result of expression tests using various promoters of *S. cerevisiae*, expression using some promoters was confirmed, but the intensity thereof was not sufficient. Accordingly, it was predicted that there is a unique expression control mechanism of the YBC strain alone, so the promoter exclusively for the YBC strain was discovered and used. Specifically, the expression levels of various genes in the YBC strain were measured, and the relevant promoter region (5' UTR) was cleaved to a maximum of 1 kb for genes showing strong expression in order to express the target gene, but low expression resulted. In particular, it was confirmed that the 1 kb-cleaved promoter was almost completely ineffective for a g4423 promoter (Korea Patent No. 2,140,596), which is a strong promoter that very strongly expresses an introduced gene, rather than an inherent gene, in the YBC strain. It was determined that the distal component (UAS or enhancer), rather than the core promoter, greatly acts on the YBC gene, and thus attempts were made to increase the strength of the promoter by binding a UAS component found in a previous study to the corresponding promoter (John Blazeck et al., Biotechnology and Bioengineering, 109(11); 2884, front page 2012).

Accordingly, the present inventors have made great efforts to find a promoter suitable for expression of a foreign gene in acid-resistant yeast, and thus ascertained that a synthetic promoter, configured such that the core promoter derived from the genome of yeast having resistance to organic acids and the UAS element derived from the foreign gene are bound together, is capable of increasing expression of a target gene even when inserted at a location other than the original location of the core promoter, thus increasing the ability to produce a target product, thereby culminating in the present invention.

SUMMARY OF THE INVENTION

Technical Problem

It is an object of the present invention to provide a synthetic promoter capable of expressing a target gene at various locations in the genome in order to produce various target products with high efficiency in a recombinant acid-resistant yeast strain having the ability to produce lactic acid.

It is another object of the present invention to provide a DNA construct for expression of a target gene including the synthetic promoter and the target gene.

It is still another object of the present invention to provide a recombinant microorganism, the genome of which is introduced with the synthetic promoter or which is introduced with the DNA construct so that the expression of a target gene is controlled by the synthetic promoter.

It is yet another object of the present invention to provide a method of expressing a target gene including culturing the recombinant microorganism.

It is still yet another object of the present invention to provide a method of producing a useful material using the recombinant microorganism.

Technical Solution

In order to achieve the above objects, the present invention provides a synthetic promoter for expression of a target gene, including;
(i) a core promoter comprising the sequence of SEQ ID NO: 1 or SEQ ID NO: 2; and
(ii) an upstream activating sequence (UAS) element comprising the sequence of SEQ ID NO: 3 or SEQ ID NO: 4.

In addition, the present invention provides a DNA construct for expression of a target gene including the synthetic promoter and the target gene.

In addition, the present invention provides a recombinant microorganism, the genome of which is introduced with the synthetic promoter or which is introduced with the DNA construct so that the expression of a target gene is controlled by the synthetic promoter.

In addition, the present invention provides a method of expressing a target gene including culturing the recombinant microorganism.

In addition, the present invention provides a method of producing a useful material including:
(a) culturing the recombinant microorganism to produce a useful material by expression of a target gene; and
(b) obtaining the produced useful material.

In addition, the present invention provides a synthetic promoter for expression of a target gene in a YBC strain or a recombinant strain derived from the YBC strain, including:
(i) a core promoter comprising a TATA box; and
(ii) an upstream activating sequence (UAS) element comprising the sequence of SEQ ID NO: 3 or SEQ ID NO: 4.

In addition, the present invention provides a recombinant strain having the ability to produce lactic acid, in which a PDC gene encoding pyruvate decarboxylase and a promoter of the PDC gene are both removed from the genome of an acid-resistant yeast YBC strain (KCTC13508BP), and the synthetic promoter and a gene encoding lactate dehydrogenase are introduced at a location from which the PDC gene is removed, so that an expression of lactate dehydrogenase is regulated via the synthetic promoter.

In addition, the present invention provides a method of producing lactic acid including:
(a) culturing the recombinant strain to produce lactic acid; and
(b) obtaining the produced lactic acid.

Advantageous Effects

When the synthetic promoter according to the present invention is applied, various useful materials, particularly organic acids, can be produced with high efficiency using acid-resistant microorganisms, and moreover, organic-acid fermentation can be performed with the ability to produce organic acids similar to that of bacterial fermentation while a neutralizer used in conventional bacterial fermentation is used in a very small amount, thereby greatly reducing fermentation costs and downstream purification processing costs.

DETAILED DESCRIPTION OF THE INVENTION

Figure 1:
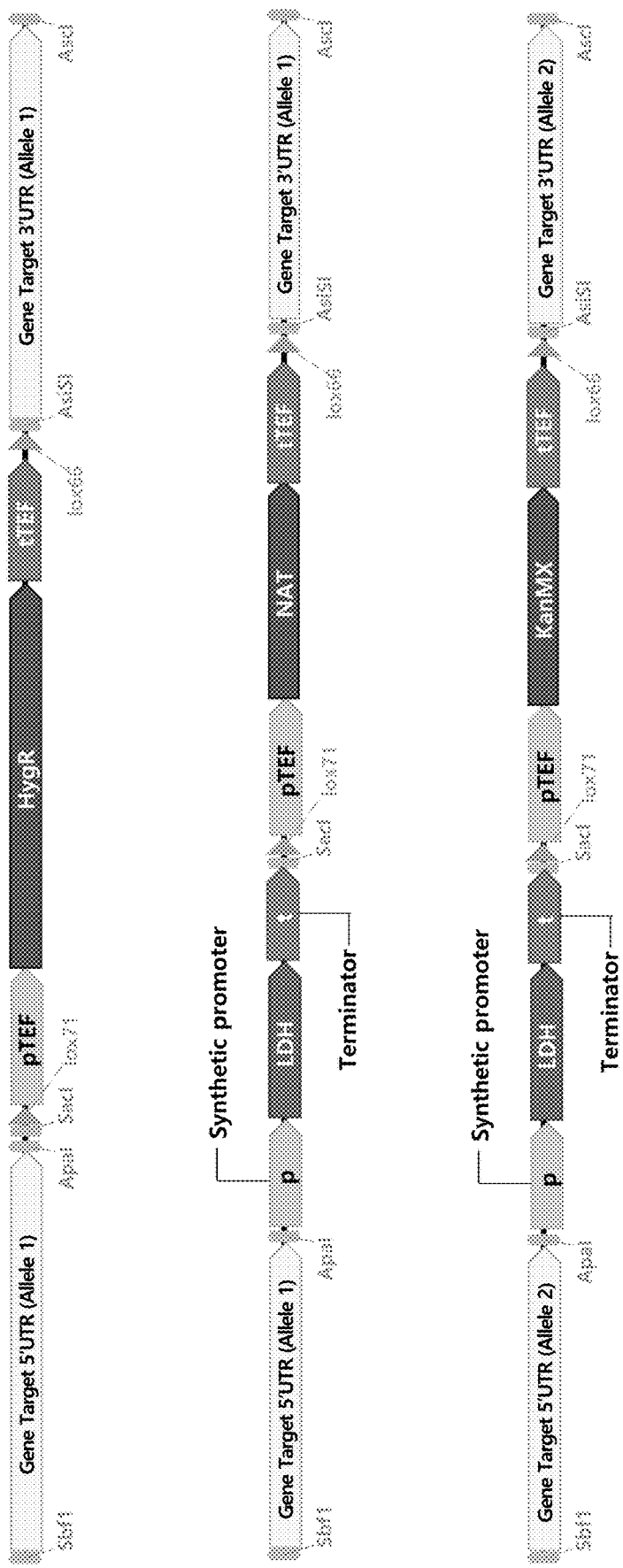
FIG. 1 shows examples of a deletion cassette for use in inserting a target gene including LDH using a synthetic promoter of the present invention by deleting a target gene including a g3002-1 (PDC1) gene from the genome of a YBC strain in the present invention or deleting the corresponding gene.

Unless otherwise defined, all technical and scientific terms used herein have the same meanings as those typically understood by those skilled in the art to which the present invention belongs. Generally, the nomenclature used herein is well known in the art and is typical.

According to the present invention, a core promoter region in an acid-resistant yeast YBC strain (KCTC13508BP) is obtained by identifying the TATA box location in the 5'-UTR of an ORF, and 2 or 3 copies of the UAS (upstream activating sequence) element of a CLB2 (mitotic cyclin) gene or a CIT1 (mitochondrial citrate synthase) gene are linked upstream of the core promoter so as to activate the same as an AT-rich region, thereby constructing a synthetic promoter in which the core promoter is strengthened. Since the UAS element may also control the expression intensity depending on the number of copies thereof, it is possible to control the expression level while maintaining the properties of the corresponding core promoter by changing the currently available number of copies of the UAS.

As the core promoter, not only the core promoter extracted from the YBC strain but also the core promoter region of the known promoter of *S. cerevisiae* are tested, so the activity thereof is determined. Various groups of combinations may be further expanded by applying a promoter derived from *S. cerevisiae*, in addition to those derived from the YBC strain.

When a useful material including lactic acid is produced from the recombinant acid-resistant yeast using the synthetic promoter, a desired target gene may be strongly expressed, thus greatly increasing the production of the useful material. In particular, the promoter of the present invention is capable of expressing the corresponding gene while controlling the expression intensity using a combination of promoters even in the presence of pathways composed of relevant useful-material-producing genes, making it possible to diversify the products of acid-resistant microorganisms compared to when using a conventional promoter existing in the inherent genome. According to the present invention, when various useful materials, particularly organic acids, are produced with high efficiency using acid-resistant microorganisms, organic-acid fermentation may be performed with the ability to produce an organic acid similar to that of bacterial fermentation while a neutralizer used in conventional bacterial fermentation is used in a very small amount, thereby greatly reducing fermentation costs and downstream purification processing costs.

In addition, the present invention provides a method capable of independently using various promoters derived from acid-resistant strains by enhancing the expression thereof, whereby various target genes may be strongly expressed using this promoter in different kinds of yeast, thus developing various promoter libraries in yeast.

Accordingly, an aspect of the present invention pertains to a synthetic promoter for expression of a target gene, including:

(i) a core promoter comprising the sequence of SEQ ID NO: 1 or SEQ ID NO: 2; and (ii) a UAS (upstream activating sequence) element comprising the sequence of SEQ ID NO: 3 or SEQ ID NO: 4.

TABLE 1

| SEQ ID NO: | Description | Sequence |
| --- | --- | --- |
| 1 | ADH gene (g4423) core promoter (allele 1) | TATATAAATGCAATTAATTGATTGTTCCTGTCACATAATTTTT TTTGTTTGTTACCTTTATTCTTTATCCATTTAATTTATTTCTT GTATCTTTCTTTTCTATTTCTCTTTTCTGTTTAATCTCACCGT ACACATATATATCCATATATCAATACAAATAAAAATCATTTAA AA |
| 2 | ADH gene (g4423) core promoter (allele 2) | TATATAAATGCAATTAATTGATTGTTCCTGTCACATAATTTTT TTTGTTTGTTACCTTTATTCTTTATCCATTTAGTTTAGTTCTT ATATCTTTCTTTTCTATTTCTCTTTTTCGTTTAATCTCACCGT ACACATATATATCCATATATCAATACAAATAAAAATCATTTAA AA |
| 3 | UAS: CIT | TAGAGATTACTACATATTCCAACAAGACCTTCGCAGGAAAGTA TACCTAAACTAATTAAAGAAATCTCCGAAGTTCGCATTTCATT GAACGGCTCAATTAATCTTTGTAAATATGAGCGTTTTTACGTT |

TABLE 1-continued

| SEQ ID NO: | Description | Sequence |
|---|---|---|
| | | CACATTGCCTTTTTTTTATGTATTTACCTTGCATTTTTGTGC<br>TAAAAGGCGTCACGTTTTTTTCCGCCGCAGCCGCCCGGAAATG<br>AAAAGTATGACCCCCGCTAGACCAAAAATACTTTTGTGTTATT<br>GGAGGATCGCAATCCCT |
| 4 | UAS: CLB | AGTGGAATTATTAGAATGACCACTACTCCTTCTAATCAAACAC<br>GCGGAAATAGCCGCCAAAAGACAGATTTTATTCCAAATGCGGG<br>TAACTATTTGTATAATATGTTTACATATTGAGCCCGTTTAGGA<br>AAGTGCAAGTTCAAGGCACTAATCAAAAAAGGAGATTTGTAAA<br>TATAGCGACCGAATCAGGAAAAGGTCAACAACGAAGTTCGCGA<br>TATGGATGAACTTCGGTGCCTGTCC |

More specifically, in the present invention, the core promoter sequence is extracted from g4423 (ADH gene) and g2947 (CYB2 gene) in the acid-resistant yeast YBC strain (KCTC13508BP), and 1 to 3 copies of the UAS element of the CLB gene or of the UAS element of the CIT gene are linked therewith so as to activate the same, thereby constructing a promoter that expresses a target gene and a plasmid that enables the promoter to operate in the YBC strain.

According to the present invention, UAS element are located 1 to 4 times repeatedly upstream of the core promoter. 1 to 4 copies of the UAS element may be located upstream of the core promoter.

According to the present invention, the synthetic promoter is preferably for expression of a target gene in a yeast strain, and more preferably for expression of a target gene in acid-resistant yeast.

According to the present invention, the acid-resistant yeast may be yeast having acid resistance selected from the group consisting of the genus *Saccharomyces, Kazachstania Saccharomyces*, and the genus *Candida*.

According to the present invention, the core promoter sequence is extracted from the known promoter of *S. cerevisiae*, and one, two or three sequences of the UAS element including CLB or CIT are linked therewith so as to activate the same, thereby constructing a promoter that operates to express the target gene in the YBC strain.

Accordingly, another aspect of the present invention pertains to a synthetic promoter for expression of a target gene in a YBC strain or a recombinant strain derived from the YBC strain, including:
(i) a core promoter including a TATA box; and
(ii) a UAS (upstream activating sequence) element comprising the sequence of SEQ ID NO: 3 or SEQ ID NO: 4.

In the synthetic promoter of the present invention, the core promoter is a core promoter for the gene located in the genome of acid-resistant yeast.

According to the present invention, the acid-resistant yeast may be yeast having acid resistance selected from the group consisting of the genus *Saccharomyces, Kazachstania Saccharomyces*, and the genus *Candida*, and the core promoter may be a core promoter (SEQ ID NO: 29) of *S. cerevisiae* TEF1 or a core promoter (SEQ ID NO: 33 or SEQ ID NO: 34) of the CYB2 gene (g2947 gene) of the YBC strain.

In an embodiment of the present invention, there is provided a promoter that operates in YBC to express the target gene by linking 1 to 3 copies of the UAS element of the CLB gene or the UAS element of the CIT gene with the core promoter extracted from the acid-resistant yeast YBC strain (KCTC13508BP) and *S. cerevisiae* so as to activate the same. Moreover, this promoter may be designed to be introduced at a target site in the genome of YBC through general homologous recombination. Also, this promoter allows the target gene to be expressed with high expression efficiency at the target site, and the expression efficiency may be regulated by adjusting the number of copies of UAS.

Still another aspect of the present invention pertains to a DNA construct for expression of a target gene including the synthetic promoter and the target gene.

Yet another aspect of the present invention pertains to a recombinant microorganism, the genome of which is introduced with the synthetic promoter or which is introduced with the DNA construct so that the expression of a target gene is controlled by the synthetic promoter.

According to the present invention, the recombinant microorganism may be characterized in that a gene encoding an enzyme having the ability to produce a useful material is introduced as a target gene.

Still yet another aspect of the present invention pertains to a method of expressing a target gene including culturing the recombinant microorganism.

A further aspect of the present invention pertains to a method of producing a useful material, including:
(a) culturing the recombinant microorganism to produce a useful material by expression of a target gene; and
(b) obtaining the produced useful material.

Still a further aspect of the present invention pertains to a recombinant strain having the ability to produce lactic acid, in which a PDC gene encoding pyruvate decarboxylase and a promoter of the PDC gene are both removed from the genome of an acid-resistant yeast YBC strain (KCTC13508BP), and the synthetic promoter and a gene encoding lactate dehydrogenase are introduced at the location from which the PDC gene is removed, so the expression of lactate dehydrogenase may be controlled via the synthetic promoter.

Yet a further aspect of the present invention pertains to a method of producing lactic acid, including:
(a) culturing the recombinant strain to produce lactic acid; and
(b) obtaining the produced lactic acid.

The acid-resistant yeast consumes sugar at a fast rate even at an acidic pH, exhibits a high growth rate, and converts the consumed sugar into a product under fermentation conditions. In a previous study by the present inventors, as yeast having these characteristics, the acid-resistant yeast YBC strain (KCTC13508BP) is selected from various yeast libraries, and the acid-resistant yeast YBC strain (KCTC13508BP) is a strain that exhibits high growth potential and sugar consumption rate even at a lactic acid concentration of 40 g/L to 80 g/L (Korean Patent No. 2,140,597).

In a previous invention by the present inventors, the metabolic network is regulated to increase the ability to produce lactic acid and decrease the ability to produce ethanol in the acid-resistant yeast YBC strain, and thus, the gene encoding alcohol dehydrogenase and the gene encoding pyruvate decarboxylase are deleted from the YBC strain, and the gene encoding the cytochrome b2 enzyme, which converts lactate into pyruvate, is deleted from the strain into which the lactate dehydrogenase gene is introduced, thereby constructing a recombinant strain having the ability to produce lactic acid (Korean Patent Application No. 2018-0119721).

In addition, the present inventors produced a recombinant strain from which the gene encoding glycerol 3-phosphate dehydrogenase, which converts dihydroxyacetone phosphate into glycerol 3-phosphate, is deleted in order to suppress glycerol production in the recombinant strain constructed above (Korean Patent Application No. 2020-0046779).

In a previous application by the present inventors, in order to restore lactic acid resistance of the recombinant strain, the recombinant strain was subcultured in a medium containing lactic acid at various concentrations up to about 80 g/L, a strain having high lactic acid resistance was selected, and the foreign lactate dehydrogenase gene substituted for the PDC gene locus of the selected strain was substituted with a lactate dehydrogenase gene derived from *S. epidermidis*, thereby constructing a new recombinant strain, indicating that this recombinant strain has both high lactic acid resistance and high ability to produce lactic acid, and moreover is capable of inhibiting the ability to produce ethanol and the ability to produce glycerol (Korean Patent Application No. 2020-0077331).

According to the present invention, when introducing individual useful material production pathways to increase the ability of the previously constructed recombinant strains to produce lactic acid and utilize acid resistance to produce a variety of useful materials, particularly bioactive compounds including organic acids, alcohols and aldehydes, in addition to the method of using the inherent promoter of the acid-resistant strain, a synthetic promoter capable of controlling the expression intensity in the genome and expressing the target gene with various intensities and variations was constructed.

In an embodiment of the present invention, there is provided a method capable of maintaining the properties of the core promoter while controlling the performance of the core promoter depending on the number of copies of UAS, in which the location of the TATA box is identified in the upstream 5'-UTR of the g4423 (ADH) gene locus of the acid-resistant yeast YBC strain (KCTC13508BP), and the core promoter sequence including the transcription start site is found and linked to 1, 2 or 3 copies of CIT or CLB, as the UAS element.

Also, in another embodiment of the present invention, there is provided a recombinant strain having the ability to produce lactic acid introduced into YBC by introducing the promoter into a uracil auxotroph plasmid to express the LDH gene, in which the gene producing lactic acid, including LDH, and related genes capable of producing other useful products are introduced into the genome at a desired location of a YBC strain or a YBC mutant strain using the promoter described above.

In still another embodiment of the present invention, a strain is constructed in a manner in which the gene encoding pyruvate decarboxylase and the related promoter are deleted from YBC, and another target gene, including *Bos taurus*-derived LDH, is introduced with high activity at the target genome location including the pyruvate decarboxylase location of the YBC strain using the above synthetic promoter or modified promoters thereof.

According to the present invention, the core promoter region of the 5'-UTR of the g4423 (ADH) gene may be comprising the sequence of SEQ ID NO: 1 and SEQ ID NO: 2, and the CIT and CLB regions linked with the core promoter may be comprising the sequence of SEQ ID NOS: 3 and 4, respectively, and these may be actively linked to constitute the promoter of the present invention. For example, 2CIT-pg4423, which is a synthetic promoter linked with two CITs, is comprising the sequence of SEQ ID NO: 5.

The promoter of the present invention constitutes a DNA construct that is introduced into yeast along with the gene encoding the target protein. Such a DNA construct includes a construct suitable for a variety of known yeast transformation methods, and examples of the DNA construct for homologous recombination are shown in FIG. 1.

The promoter region of the DNA construct may be composed of the synthetic promoter including two CITs and the core promoter of g4423, and the LDH gene is used as an example of the target gene. In particular, *Bos taurus*-derived LDH (BtLDH) is used as a target gene and *S. cerevisiae*-derived CYC1t is used as a terminator, so a cassette for gene insertion may be constructed by deleting the g3002-1 gene, among various genome locations of the YBC strain. To this end, an example in which BtLDH as the target gene is linked with 2CIT-pg4423 and a CYC1t terminator is comprising the sequence of SEQ ID NO: 6. In addition, when a different kind of target DNA is inserted into the cassette, when a region for each target genome location is inserted into the homologous recombination region, or when a differently constituted synthetic promoter is inserted into the synthetic promoter region, a cassette for gene insertion suitable therefor may be made, which is well known to those skilled in the art. As an example of a differently constituted synthetic promoter, the 3CIT-pTEF1 promoter composed of CIT as UAS, an *S. cerevisiae*-derived TEF1 gene, and a core promoter is comprising the sequence of SEQ ID NO: 7, and an example in which BtLDH as a target gene and a CYC1 terminator are linked is comprising the sequence of SEQ ID NO: 8.

According to the present invention, the cassette may include a promoter comprising the sequence of the nucleotide sequence of SEQ ID NO: 5 or SEQ ID NO: 7, and the cassette may include various target genes, and may be introduced into the genome of various kinds of yeast including YBC by changing the HR of FIG. 1.

The promoter of the present invention may constitute a DNA construct that is introduced into yeast along with a gene encoding a target protein. Such a DNA construct includes a construct suitable for a variety of known yeast transformation methods, and examples of the DNA construct for introduction in the form of a plasmid are comprising the sequence of SEQ ID NO: 9 and SEQ ID NO: 10. The DNA construct includes the synthetic promoter, particularly the synthetic promoter including two CITs and the core promoter of g4423, and in order to express various target genes, for example, LpLDH as a target gene, in the YBC strain, a vector in the form of a plasmid expressing uracil as an auxotroph marker may be constructed, and is comprising the sequence of SEQ ID NO: 9. Another example of the synthetic promoter is a synthetic promoter including three CITs, an *S. cerevisiae*-derived TEF1 gene, and a core promoter, and in order to express various target genes, particularly LpLDH as a target gene, in the YBC strain, a vector in the form of a plasmid expressing uracil as an auxotroph marker may be constructed, and is comprising the sequence of SEQ ID NO: 10. In addition, when a different kind of target DNA is inserted into this cassette, when an auxotroph marker for introduction into YBC is modified, or when a differently constituted synthetic promoter is inserted into the synthetic promoter region, a cassette for gene insertion suitable therefor may be made, which is well known in the art.

According to the present invention, the recombinant strain may be a strain genetically engineered to produce lactic acid as described above or a strain engineered to produce other useful products.

An organic acid may be produced by culturing the recombinant microorganism introduced with the DNA construct of the present invention.

As used herein, the term "homology" refers to the identity percentage between two comparable amino acids or polynucleotide moieties. Also, the term "similarity" refers to the extent to which sequences are determined to be functionally or structurally identical based on amino acid or polynucleotide sequences through a comparison window. Sequence homology or similarity may be determined by comparing sequences using standard software, for example, the BLASTN and BLASTX programs, developed based on BLAST (Proc. Natl. Acad. Sci. USA, 90, 5873-5877, 1993).

According to the present invention, the g4423 core promoter preferably has a sequence showing at least 90%, at least 92%, at least 93%, at least 95%, at least 97%, at least 98%, at least 99%, or 100% sequence homology with the sequence of SEQ ID NO: 1 or SEQ ID NO: 2, while including a TATA box and a transcription start sequence.

If a promoter has at least 90% homology with the g4423 promoter of the present invention and shows equivalent expression efficiency in the YBC genome or different kinds of yeast, it may be said to be a substantially identical promoter.

In some cases, the g4423 promoter according to the present invention may be mutated using a technique known in the art in order to increase the expression efficiency of the target gene.

CIT and CLB, which are identically used UAS regions, preferably have sequences showing at least 90%, at least 92%, at least 93%, at least 95%, at least 97%, at least 98%, at least 99%, or 100% sequence homology with the sequences of SEQ ID NOS: 2 and 3.

If a promoter has at least 90% homology with the UAS region of the present invention and shows equivalent expression efficiency in the YBC genome or in different kinds of yeast by binding to the above-specified core promoter, the known promoter or the promoter having at least 90% homology therewith, it may be said to be a substantially identical promoter.

In some cases, the promoter including the UAS region according to the present invention may be mutated using a technique known in the art in order to increase the expression efficiency of the target gene.

According to the present invention, the recombinant yeast may be characterized by having acid resistance, and in order to construct acid-resistant recombinant yeast suitable for the present invention, it is preferable to use host yeast having resistance to organic acids.

The acid-resistant yeast may be yeast having acid resistance selected from the group consisting of the genus *Saccharomyces*, *Kazachstania Saccharomyces*, and the genus *Candida*, and may be selected from the group consisting of, for example, *Saccharomyces cerevisiae*, *Kazachstania exigua*, *Kazachstania bulderi*, and *Candida humilis*, but is not limited thereto.

As used herein, the term "acid-resistant yeast" refers to yeast capable of maintaining a biomass consumption rate (a sugar consumption rate, etc.) of at least 10% or a specific growth rate of at least 10% when the medium contains 1 M or more of an organic acid (especially lactic acid) at a pH less than the pKa value of the organic acid, compared to when the medium does not contain an organic acid. More specifically, According to the present invention, the acid-resistant yeast is defined as yeast capable of maintaining a biomass consumption rate (a sugar consumption rate, etc.) of at least 10% or a specific growth rate of at least 10% at a pH of 2 to 4, compared to a pH of 5 or higher.

The recombinant yeast according to the present invention may be constructed by inserting the gene into the chromosome of the host yeast according to a typical method, or by introducing a vector including the gene into the host yeast.

As the host yeast, host cells having high DNA introduction efficiency and high expression efficiency of introduced DNA are typically used. In an embodiment of the present invention, acid-resistant yeast is used, but the present invention is not limited thereto, and any kind of yeast may be used, so long as the target DNA is capable of being sufficiently expressed.

The recombinant yeast may be constructed using any transformation method. As used herein, the term "transformation" refers to the introduction of DNA into a host such that the DNA becomes replicable either as an extrachromosomal factor or by chromosomal integration, and to a phenomenon by which exogenous DNA is introduced into a cell to artificially cause a genetic change. Typical examples of the transformation method include electroporation, a lithium acetate-PEG method, and the like.

In addition, as a method of inserting a gene into the chromosome of a host microorganism in the present invention, any typically known genetic engineering method may be used, and examples thereof may include methods using a retroviral vector, adenoviral vector, adeno-associated viral vector, herpes simplex virus vector, fox virus vector, lentiviral vector, non-viral vector, and the like. As used herein, the term "vector" refers to a DNA molecule containing a DNA sequence operably linked to a suitable expression control sequence capable of expressing DNA in a suitable host. The vector may be a plasmid, a phage particle, or a potential genomic insert. Upon transformation into an appropriate host, the vector may replicate and function independently of the host genome, or in some cases may be integrated into the genome itself. A plasmid is currently the most commonly used form of vector, and linearized DNA is also a form commonly used for genome integration in yeast.

A typical plasmid vector includes (a) a replication origin that enables efficient replication to include the plasmid vector per host cell, (b) an antibiotic resistance gene or auxotroph marker gene to allow selection of host cells transformed with the plasmid vector, and (c) a restriction enzyme cleavage site that allows a foreign DNA fragment to be inserted. Even when an appropriate restriction enzyme cleavage site is absent, the vector and foreign DNA may be easily ligated (Gibson assembly) using a synthetic oligonucleotide adapter or linker according to a typical method, and, as necessary, a method of synthesizing and using the entire sequence of interest is also typically employed.

Moreover, the gene is said to be "operably linked" when placed in a functional relationship with another nucleic acid sequence. It may be a gene and control sequence(s) linked in such a manner that an appropriate molecule (e.g. a transcriptional activation protein), when bound to the control sequence(s), allows for gene expression. For example, DNA for a pre-sequence or secretory leader is operably linked to DNA for a polypeptide when expressed as a preprotein that participates in secretion of the polypeptide, a promoter or enhancer is operably linked to a coding sequence when affecting the transcription of the sequence, a ribosome-binding site is operably linked to a coding sequence when affecting the transcription of the sequence, or a ribosome-binding site is operably linked to a coding sequence when located to facilitate translation.

In general, "operably linked" means that the linked DNA sequence is in contact therewith, and also that the secretory leader is in contact therewith and is present in the reading frame. However, the enhancer need not be in contact therewith. The linkage of these sequences is accomplished by ligation at convenient restriction enzyme sites. When no such site exists, a synthetic oligonucleotide adapter or linker is used according to a typical method.

It should be clearly understood that not all vectors function equally in expressing the DNA sequences of the present invention. Likewise, not all hosts function equally in the same expression system. However, those skilled in the art may make appropriate selection from among various vectors, expression control sequences, and hosts without departing from the scope of the present invention without undue experimental burden. For example, when selecting a vector, the host has to be taken into consideration. This is because the vector has to be replicated therein. The number of copies of the vector, the ability thereof to control the number of copies, and the expression of other proteins encoded by the vector, for example antibiotic markers, also have to be taken into consideration.

In the present invention, the carbon source may be at least one selected from the group consisting of glucose, xylose, arabinose, sucrose, fructose, cellulose, galactose, glucose oligomer, and glycerol, but is not limited thereto.

In the present invention, culture may be carried out under conditions such that microorganisms, for example *Escherichia coli* and the like, do not function any more (e.g. metabolite production is impossible). For example, culture may be conducted at a pH of 1.0 to 6.5, preferably a pH of 1.0 to 6.0, and more preferably a pH of 2.6 to 4.0, but the present invention is not limited thereto.

Moreover, in the present invention, the target product and the related gene include, in addition to lactic acid, organic acids such as succinic acid, adipic acid, acrylic acid, methyl methacrylic acid, 3-hydroxypropionic acid, acetic acid, butyric acid, isobutyric acid, valeric acid, hexanoic acid, iso-valeric acid, malic acid, fumaric acid, and itaconic acid, and a wild-type acid-resistant strain is yeast that is able to ferment ethanol at a high concentration, and is thus advantageous for the production of other alcohols, making it possible to develop high-production strains through genetic engineering in order to produce alcohols such as butanediol, propanediol, propanol, butanol, isobutanol, hexanol and the like with high efficiency.

A better understanding of the present invention may be obtained through the following examples. However, these examples are merely set forth to illustrate the present invention, and are not to be construed as limiting the scope of the present invention, as will be apparent to those skilled in the art.

Example 1: Confirmation of Performance of Cleaved YBC Promoter in Acid-Resistant Yeast Strain Using a YBC strain (KCTC13508BP), which is an acid-resistant yeast strain, and a strain derived from the YBC strain and subjected to genetic engineering and forced evolution (e.g. KCTC 14215BP), promoters capable of controlling the expression intensity and expression pattern of a target gene were discovered.

Various promoters derived from *S. cerevisiae* (*S. cerevisiae* S288C) and the 1 kb-cleaved region of 5' UTR of genes, which were judged to be main genes based on annotation in the genome of YBC, were linked to a gene to be expressed. For the gene expressed by the promoter, an mCherry gene (SEQ ID NO: 31) was selected. The mCherry gene was well expressed in *S. cerevisiae*, and it was predicted that there would be an advantage of being able to easily measure the strength of the promoter based on color development because the intensity of color development varies depending on the type of protein by the strength of the promoter.

However, in the YBC strain, it was difficult to measure fluorescence in all transformed colonies. Although there was the possibility that the expression of mCherry itself did not occur well, there was also the possibility that very weak expression occurred using the promoters that were tested. Therefore, in order to compare the strength of the promoters, qRT-PCR was performed.

The experimental method was as follows. Using restriction sites (AscI & SbfI), each promoter to be tested was introduced into the promoter region of a vector having 5' and 3' UTRs of Ura3 as homologous recombination sites and expressing mCherry. The target promoters were ENO1/2, ILV5, EFT2, FBA1, ADH1 (g4423), PDC1, PGI1, TDH3, TEF1, PYK1 and GPM1 derived from YBC, in which the 1 kb-cleaved region of 5' UTR of each gene was cloned through PCR and used, and also, promoters such as GPM1, ADH1, PYK1, TPI1, ENO2, TDH3 and TEF1 derived from *S. cerevisiae* were used. After inserting the corresponding region into the YBC gene, each insertion was confirmed through PCR. The cells including the target promoter were cultured, followed by RNA prep, cDNA synthesis, and then real-time PCR. The concentration of each protein was measured separately, and the expression levels at different concentrations were compared.

Figure 2:
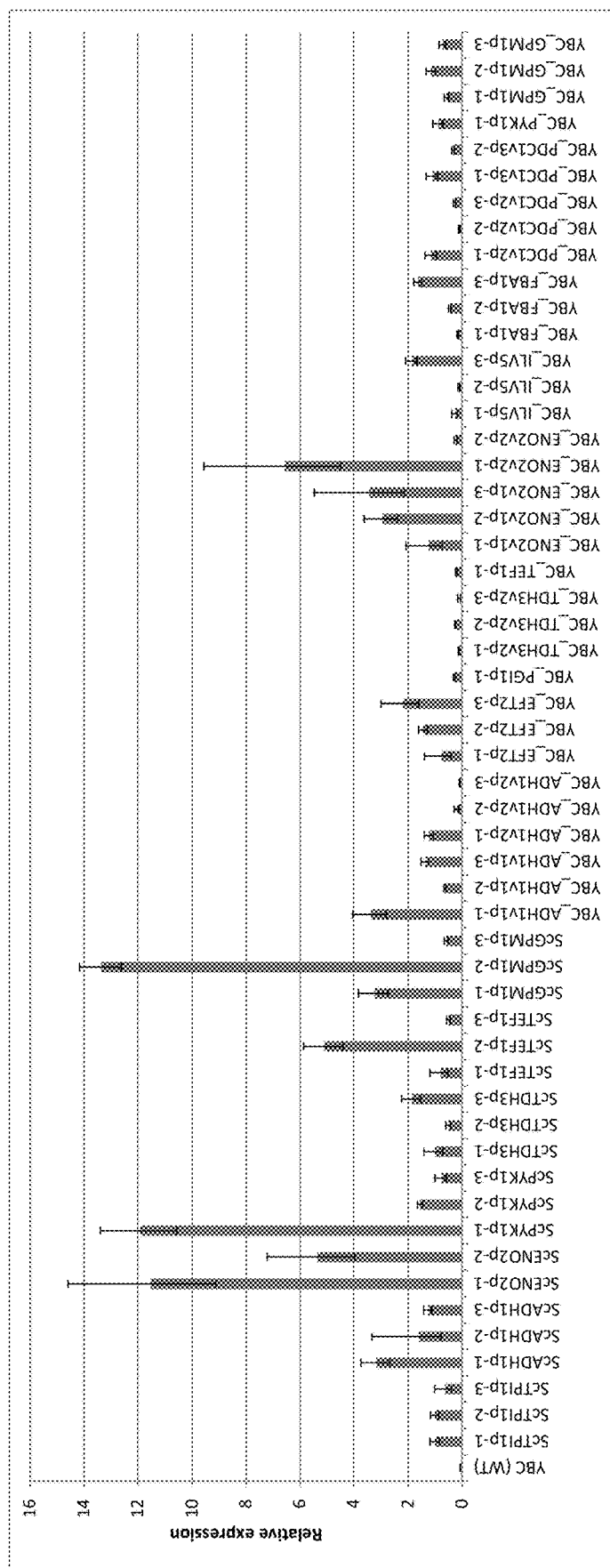
FIG. 2 shows the results of measurement of expression levels through qRT-PCR after expression of the mCherry gene in the YBC genome using promoters derived from *S. cerevisiae* and a variety of 1 kb-cleaved inherent promoter regions of the YBC strain.

FIG. 2 shows the expression levels using the corresponding promoters based on the expression level of mCherry, expressed by TPI1p of *S. cerevisiae*. Although there was a difference in the expression level for each promoter, the expression level did not exceed a maximum of 13. Considering that an expression level hundreds of times that of a housekeeping gene is the general expression level of a strong promoter when expressing the original target gene of a promoter using an inherent promoter (reference is made to the expression level of the g4423 gene in FIG. 6 of Korean Patent No. 2,140,596), it was confirmed that a sufficient expression level could not be obtained with the tested promoters.

Example 2: Comparison of Performance of Strong g4423 Promoter and 1 kb-Cleaved g4423 Promoter in Acid-Resistant Yeast Strain Since there is a possibility that the expression of the mCherry gene in the YBC strain is weak, in the present example, a g4423 promoter and an MCR gene, the strong expression of which was confirmed in YBC, were used.

The g4423 gene in the YBC genome was strongly expressed, and the MCR gene was expressed using the corresponding promoter. As a comparative group, the 1 kb-cleaved promoter region of g4423 was used to express the same MCR gene in the YBC genome. Here, the promoter and the MCR gene were introduced at the ALD2 location for the target genome.

The strain was constructed as follows.

First, when introducing MCR at the g4423 location, a strain from which the g4423 gene (SEQ ID NO: 11 and SEQ ID NO: 12), which is the main ADH gene of the YBC strain, was removed and to which the MCR gene of SEQ ID NO: 13 derived from Sulfolobales archaeon Acd1 was introduced at the g4423 location was constructed, and based on the information of g4423 and UTR thereof, a gene cassette from which the ORF of each gene was removed and which included 5' and 3' UTRs was constructed and used as donor DNA. For each allele of g4423, the corresponding 5' UTR is comprising the sequence of SEQ ID NO: 14 and SEQ ID NO: 15, and the 3' UTR is comprising the sequence of SEQ ID NO: 16 and SEQ ID NO: 17. Here, the construction of donor DNA was performed using a cloning method using restriction enzymes, a Gibson assembly method, or a method using gene synthesis, as described above.

As a comparative group, a strain in which the promoter of g4423 was cleaved to 1 kb (SEQ ID NO: 18 and SEQ ID NO: 19), linked with the same MCR gene of SEQ ID NO: 13, and introduced at the ald2 location of the YBC gene was constructed. For each allele at the ald2 location, the corresponding 5' UTR was comprising the sequence of SEQ ID NO: 20 and SEQ ID NO: 21, and the 3' UTR was comprising the sequence of SEQ ID NO: 22 and SEQ ID NO: 23. Here, the construction of donor DNA was performed using a cloning method using restriction enzymes, a Gibson assembly method, or a method using gene synthesis, as described above.

The strain thus constructed was cultured at 30° C. and 150 rpm for 120 hours in a YP (10 g/L of a yeast extract and 20 g/L of peptone) medium supplemented with 15 µM cerulenin and 40 g/L of glucose.

Figure 3:
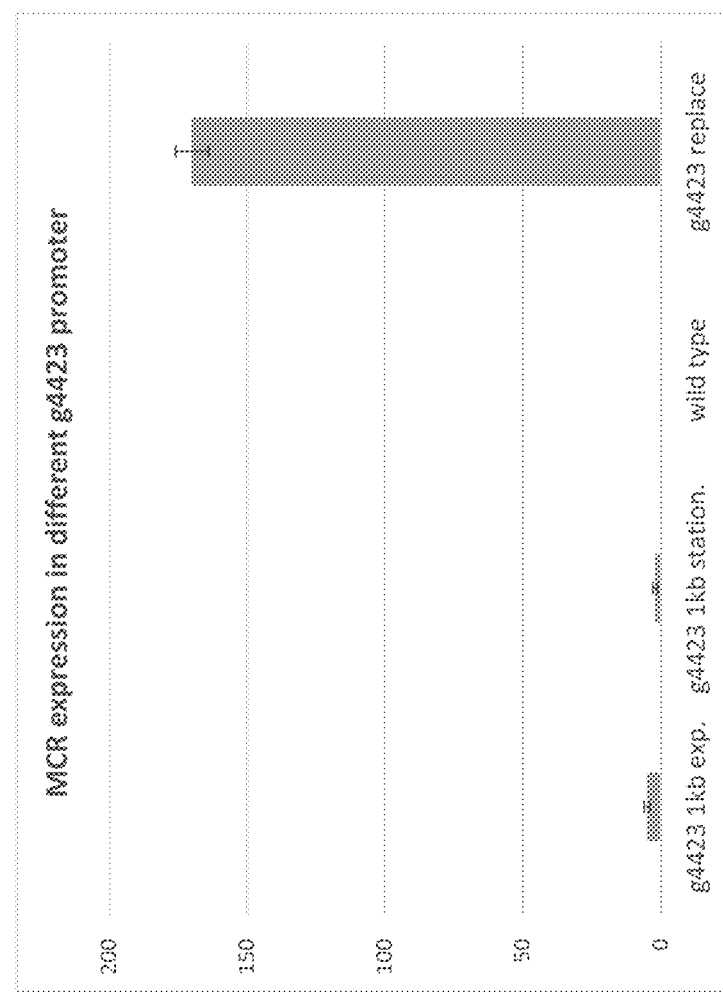
FIG. 3 shows the results of comparison of the expression levels of the MCRsa1 gene upon expression of the MCRsa1 gene in the YBC genome using a g4423 natural promoter as the high-performance promoter of YBC in which the MCRsa1 gene, in place of the g4423 gene, is introduced (g4423 replace), and using g4423 1 kb promoter regions expressed in the ald2 genome of YBC (exponential growth (exp.) and stationary growth (station.) of g4423 1 kb)
Figure 4A:
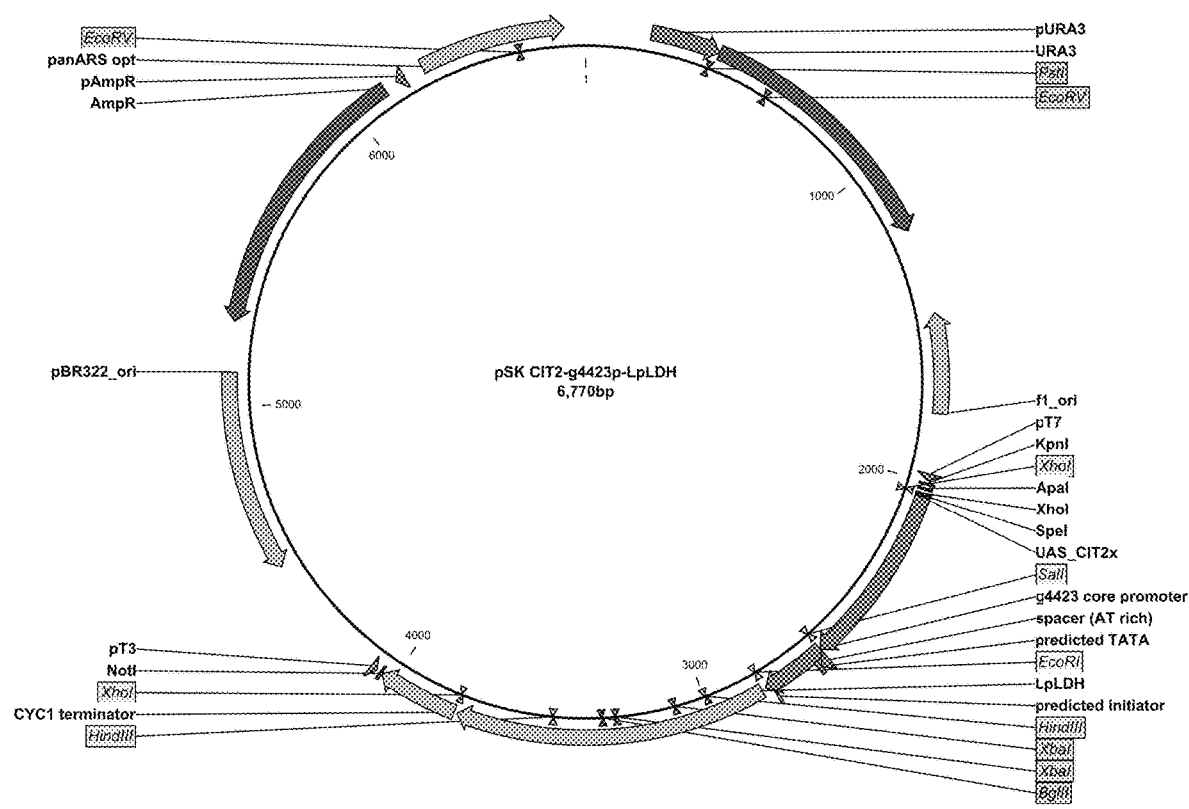
FIGS. 4A and 4B shows genetic maps for vectors when expressed in the form of a plasmid in YBC by (a) linking a YBC-derived g4423 core promoter and two CITs as UAS according to the present invention (see FIG. 4A) and (b) linking an *S. cerevisiae*-derived TEF1 promoter and three CITs as UAS (see FIG. 4B)
Figure 4B:
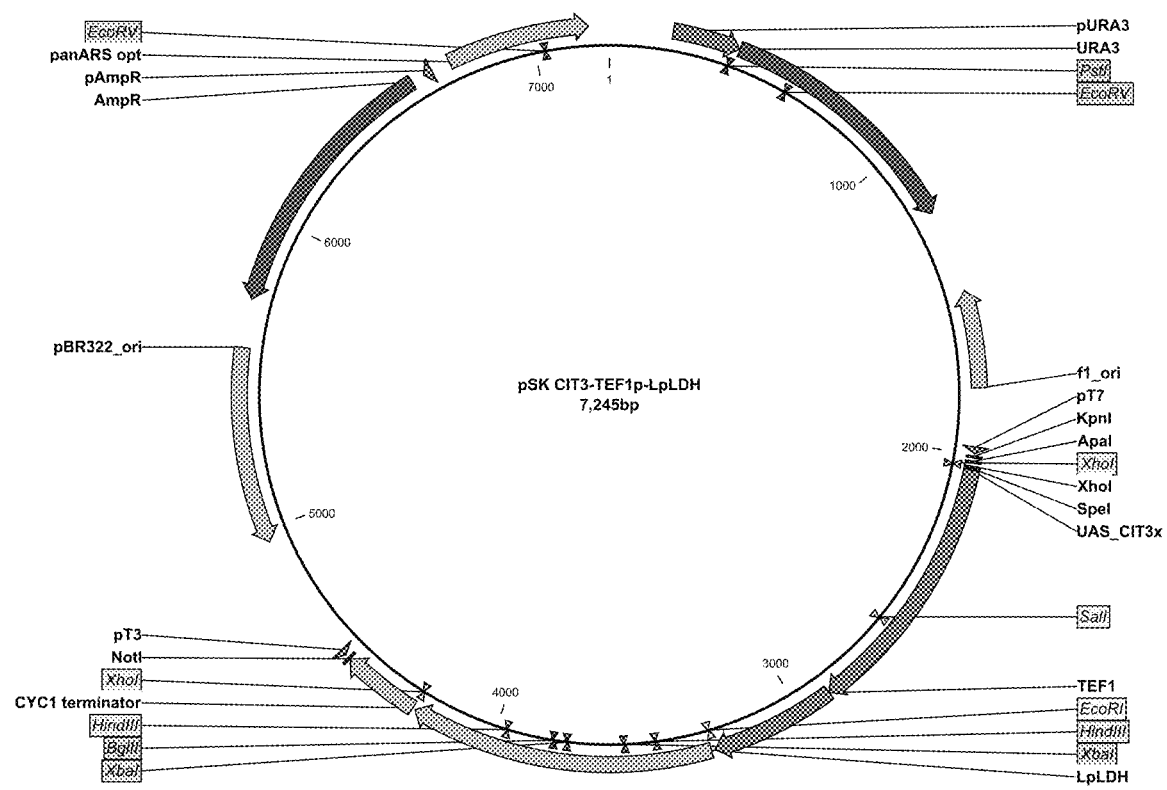

For both strains, the expression level of the MCR gene during culture was measured through qPCR, as in Example 1, and the results thereof are shown in FIG. 3.

As shown in FIG. 3, the MCR gene using the promoter of g4423 without change was strongly expressed, and it was also experimentally confirmed that fermentation of 3-hydroxypropionic acid (3-HP) at a high concentration of 710 mg/L in a flask using a glucose substrate by binding to other genes in the 3-HP-related production pathway was possible. On the other hand, the strain expressing the MCR gene with the 1 kb-cleaved promoter of g4423 exhibited a relatively very low MCR expression level, and in the 3-HP production flask experiment, performed by binding to other genes in the corresponding 3-HP pathway, it was confirmed that 3-HP having a very low concentration of 10 mg/L or less was produced at the same glucose concentration, indicating that the difference in the expression level of MCR directly affects the product concentration in the corresponding pathway.

TABLE 2

Comparison of 3-HP production by MCR gene expressed with 1 kb-cleaved promoter and inherent promoter for g4423 promoter

| | 3-HP concentration (mg/L) |
|---|---|
| g4423 1 kb-cleaved promoter | <10 |
| g4423 inherent promoter | 710 |

Therefore, it was confirmed that it is impossible to utilize the strong promoter in YBC in other genomes only with the current method of cleaving the target promoter region to 1 kb.

Example 3: Construction of g4423-Based Synthetic Promoter and Confirmation of Activity Thereof In order to use the YBC strain-derived promoter in other genomes of the corresponding strain and to enhance the performance of other promoters already used in yeast upon use thereof in YBC, a strategy to strengthen the core promoter by UAS in the form of a synthetic promoter was applied.

To this end, the core promoter region was further extracted from the 1 kb region of g4423. In the core promoter region, the common TATA box site and the initiator (transcription start site) were identified using TATA box prediction tools (Eukaryotic core promoter predictor (YAPP), ElemeNT Element Navigation Tool), and the core promoter (SEQ ID NO: 1 and SEQ ID NO: 2) including the same was selected.

UAS of each of the CLB2 (mitotic cyclin) gene and the CIT1 (mitochondrial citrate synthase) gene was selected as UAS to be used for the synthetic promoter.

2 copies of the UAS (SEQ ID NO: 3) of CIT and the UAS (SEQ ID NO: 4) of CLB were located upstream of the core promoter to construct respective promoters 2CIT-pg4423 (SEQ ID NO: 5) and 2CLB-pg4423.

In addition, 3 copies of CIT and CLB were located upstream of the promoters of TEF1 and TDH3 derived from S. cerevisiae to construct new synthetic promoters, which were named 3CIT-pTEF1 (SEQ ID NO: 7) and 3CLB-pTDH3, respectively.

In addition, a comparative group, particularly pCCW14v5 (Arun S. Rajkumar et al., Nucleic Acids Research, 44(17); e136, 2016) was used as an acid-resistant promoter reported in the literature.

In order to express the constructed promoter in the form of a plasmid in YBC, it was introduced into a vector (pSK699 (pRS426 variant) from VTT) having a uracil auxotroph marker, and the Lactobacillus plantarum-derived LDH gene (SEQ ID NO: 32) was expressed using the promoter. Among the forms introduced into the vector, the plasmid having 2 copies of CIT and a g4423 core promoter is shown in FIG. 3(a), and the sequence of the plasmid comprises the sequence of SEQ ID NO: 9. In addition, the plasmid having 3 copies of CIT and an S. cerevisiae-derived TEF1 promoter (SEQ ID NO: 29) is shown in FIG. 3(b), and the sequence of the plasmid comprises the sequence of SEQ ID NO: 10. Other promoters were constructed in similar forms and introduced into the YBC strain.

The corresponding vector had an Ura marker, and the YBC strain was made with a uracil auxotroph so that only the strain introduced with the vector was grown in the selective medium.

Flask culture evaluation was performed on the colonies selected for each plasmid, and the culture conditions were as follows. In a 250 ml flask, a yeast nitrogen base medium (without uracil) was supplemented with 50 g/L of glucose to make a total volume of 50 ml, and the microorganisms were seeded at an initial OD of 0.5 and cultured at 30° C. and 250 rpm for 24 hours.

The results of analysis of lactic acid production for flask culture are shown in Table 3 below.

TABLE 3

| Plasmid | Produced lactic acid concentration (g/L) |
|---|---|
| Control (YBC wild type) | 0.184 |
| 2CIT-pg4423 | 1.07 |
| 2CLB-pg4423 | 0.016 |
| 3CIT-pTEF1 | 0.707 |
| 3CLB-pTDH3 | 0 |
| pCCW14v5 | 0.137 |

Comparison of LDH expression levels using individual synthetic promoters shown in Table 3. 2CIT-pg4423: synthetic promoter in which two CITs as UAS and a core promoter derived from YBC-derived g4423 are linked; 2CLB-pg4423: synthetic promoter in which two CLBs as UAS and a core promoter derived from YBC-derived g4423 are linked; 3CIT-pTEF1: synthetic promoter in which three CITs as UAS and a core promoter of S. cerevisiae-derived TEF1 are linked; 3CLB-pTDH3: synthetic promoter in which three CLBs as UAS and a core promoter of S. cerevisiae-derived TDH3 are linked; pCCW14v5: a reference experimental group as a previously reported acid-resistant promoter Based on the results of flask culture, the two active promoters strongly expressed LpLDH, and the selected 2CIT-pg4423 and 3CIT-pTEF1 were directly inserted into the genome of the acid-resistant strain to compare the performance thereof.

Example 4: Confirmation of Expression of 2CIT-Pg4423 and 3CIT-pTEF1 in YBC Genome Using the two promoters selected in Example 3, the YBC strain-derived promoter was expressed in the genome of the corresponding strain to confirm the performance thereof.

The YBC gene site was determined to be g3002-1, and the target gene was determined to be BtLDH. The reason why the target gene was changed from LpLDH, tested in the plasmid, to BtLDH was that a phenomenon by which the expression of LpLDH was suppressed in g3002-1 was observed, which was described in detail in an earlier patent application by the present researchers (Korean Patent Application No. 2020-0077331). It was judged that it was difficult to compare the activity of the introduced promoter due to suppression of the target gene, and a comparative experiment was performed with BtLDH, the activity of which was confirmed.

The BtLDH gene (SEQ ID NO: 30) as a target gene was located after the selected promoter, and S. cerevisiae-derived CYC1t was used as a terminator. In order to introduce this gene, the 5'-UTR and the 3'-UTR of the g3002-1 gene were utilized. In order to inhibit the activity of the inherent promoter of g3002-1, the promoter and the gene were introduced at the g3002-1 location by removing a portion of the 5'-UTR of g3002-1, or in the direction opposite the direction of the inherent promoter of g3002-1.

The strain was constructed as follows.

Specifically, when 2CIT-pg4423p or 3CIT-pTEF1 as a promoter and BtLDH as a target gene were introduced in the reverse direction at the g3002-1 location, the g3002-1 gene (SEQ ID NO: 24), which is the main PDC gene of the YBC strain, was removed, and the promoter and the BtLDH target gene, having CYC1t as a terminator, were introduced at the g3002-1 location. For introduction in the reverse direction, the complementary sequence (reverse complement, SEQ ID NO: 25) of the 3'-UTR of g3002-1 was introduced upstream (5'-UTR) of the introduced gene, the complementary sequence (reverse complement, SEQ ID NO: 26) of the 5'-UTR of g3002-1 was introduced downstream (3'-UTR) of the introduced gene, and based on this UTR information, a gene cassette in which the target gene (SEQ ID NO: 6 and SEQ ID NO: 8) was introduced in the reverse direction by removing the ORF of each gene was constructed and used as donor DNA. Here, the construction of donor DNA was performed using a cloning method using restriction enzymes, a Gibson assembly method, or a method using gene synthesis, as described above.

When introducing 2CIT-pg4423p as a promoter and BtLDH as a target gene in the forward direction at the g3002-1 location, the g3002-1 gene, which is the main PDC gene of the YBC strain, was removed, and the promoter and the target gene BtLDH, having CYC1t as a terminator, were introduced at the g3002-1 location. For introduction in the forward direction, the sequence obtained by cleaving a portion of 5'-UTR serving as an inherent promoter located upstream of the g3002-1 gene was introduced at the target site of HR to thus inactivate the inherent promoter, and the sequence obtained by cleaving a portion of 3'-UTR serving as an inherent terminator located downstream of the g3002-1 gene was introduced at the target site of HR to thus inactivate the inherent terminator. Here, the 5'-UTR and 3'-UTR sequences of g3002-1 comprises the sequence of by SEQ ID NO: 27 and SEQ ID NO: 28, respectively. Based on this UTR information, a gene cassette in which the target gene was introduced in the forward direction by removing the ORF of each gene was constructed and used as donor DNA. Here, the construction of donor DNA was performed using a cloning method using restriction enzymes, a Gibson assembly method, or a method using gene synthesis, as described above.

The performance of the g3002-1 inherent promoter was compared with that of the 3CIT-pTEF1 promoter introduced in place thereof.

Flask culture evaluation was performed on the selected colonies, and the culture conditions were as follows. Glucose was added to a YPDU medium (20 g/L of peptone, 10 g/L of a yeast extract, and 0.15 g/L of uracil) to make a final concentration of 50 g/L such that a total volume was 50 ml in a 500 ml baffled flask, after which microorganisms were seeded thereto and cultured at 30° C. and 150 rpm for 24 hours.

TABLE 4

| Promoter | Lactic acid yield relative to sugar (g/g) |
|---|---|
| g3002-1 Inherent promoter | 0.07 |
| 3CIT-pTEF1 | 0.012 |

As is apparent from Table 4, when 3CIT-pTEF1 was introduced as the promoter, it was confirmed that the expression of lactic acid in the same gene was weaker than that of the inherent promoter. However, this result is also deemed to be meaningful in that it shows that various promoters in yeast may be used in YBC, considering that it was not easy to measure the expression level in the YBC genome when other existing promoters were introduced.

In addition, the performance of the g3002-1 internal promoter was compared with that of the 2CIT-pg4423 promoter, which was introduced in the forward and reverse directions in place thereof.

Flask culture evaluation was performed on the selected colonies, and the culture conditions were as follows. Glucose was added to a YPDU medium (20 g/L of peptone, 10 g/L of a yeast extract, and 0.15 g/L of uracil) to make a final concentration of 50 g/L such that a total volume was 50 ml in a 500 ml baffled flask, after which microorganisms were seeded thereto and cultured at 30° C. and 150 rpm for 24 hours.

Figure 5:
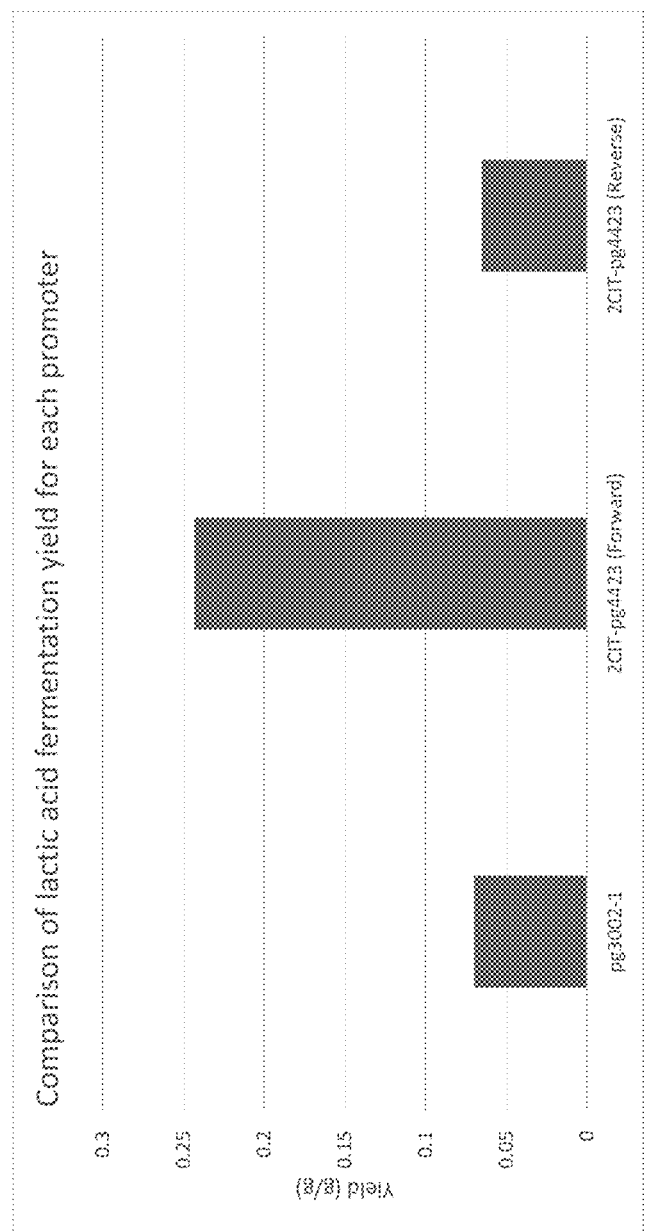
FIG. 5 shows the results of evaluation of the ability to produce lactic acid upon expression of BtLDH using a 2CIT-pg4423 promoter according to the present invention, which is introduced at the YBC g3002-1 location, from which the promoter and the terminator are removed, and, as comparative groups thereof for expressing the same BtLDH gene and comparing the amounts of lactic acid that is produced, using a YBC g3002-1 inherent promoter, and a 2CIT-pg4423 promoter introduced in the reverse direction at the same YBC g3002-1 location.

As shown in FIG. 5, BtLDH expressed using 2CIT-pg4423 exhibited high expression efficiency compared to the expression result using g3002-1, which is the inherent promoter that strongly expresses the main PDC1 gene of the YBC strain, which was clearly seen based on a difference in the production yield of lactic acid. In particular, it was confirmed that, when introduced in the forward direction by removing the inherent promoter and terminator, the expression intensity was three times greater than when using the existing promoter, indicating that the promoter of the present invention can be satisfactorily used as a strong promoter that is independently usable in YBC, which has been the goal of multiple concurrent studies. In particular, this method employing a synthetic promoter can be utilized in various ways in the future by suggesting a method of constructing various synthetic promoters using other promoters in YBC, and it is possible to control the expression intensity by changing the number of copies of UAS.

Although specific embodiments of the present invention have been disclosed in detail as described above, it will be obvious to those of ordinary skill in the art that the description is merely of preferable exemplary embodiments and is not to be construed as limiting the scope of the present invention. Therefore, the substantial scope of the present invention will be defined by the appended claims and equivalents thereof.

What is claimed is:

1. A synthetic promoter for expression of a target gene, comprising a core promoter and an upstream activating sequence (UAS) element comprising:
   (i) the sequence of SEQ ID NO: 1 or SEQ ID NO: 2 as the core promoter; and
   (ii) the sequence of SEQ ID NO: 3 as the UAS element.

2. The synthetic promoter according to claim 1, wherein the UAS element is located 1 to 4 times repeatedly upstream of the core promoter.

3. The synthetic promoter according to claim 1, wherein the promoter is for an expression of a target gene in a yeast strain.

4. The synthetic promoter according to claim 3, wherein the yeast strain is an acid-resistant yeast.

5. The synthetic promoter according to claim 4, wherein the acid-resistant yeast is a yeast having acid resistance selected from the group consisting of genus *Saccharomyces*, *Kazachstania Saccharomyces*, and genus *Candida*.

6. A DNA construct for expression of a target gene comprising the synthetic promoter according to claim 1 and a target gene.

7. A recombinant microorganism, a genome of which is introduced with the synthetic promoter according to claim 1.

8. The recombinant microorganism according to claim 7, which is a yeast having acid resistance selected from the group consisting of genus *Saccharomyces*, *Kazachstania Saccharomyces*, and genus *Candida*.

9. The recombinant microorganism according to claim 7, into which a gene encoding an enzyme is introduced as a target gene.

10. A method of expressing a target gene, comprising culturing the recombinant microorganism according to claim 7.

* * * * *